(12) United States Patent
Yamaguchi

(10) Patent No.: US 7,023,589 B2
(45) Date of Patent: Apr. 4, 2006

(54) LIGHT SOURCE DEVICE AND DEVICE FOR READING ORIGINAL

(75) Inventor: Hiroshi Yamaguchi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 1168 days.

(21) Appl. No.: 09/755,186

(22) Filed: Jan. 8, 2001

(65) Prior Publication Data

US 2001/0026369 A1   Oct. 4, 2001

(30) Foreign Application Priority Data

Jan. 12, 2000 (JP) .............................. 2000-003859
Dec. 25, 2000 (JP) .............................. 2000-392965

(51) Int. Cl.
*H04N 1/04* (2006.01)
*G06K 7/00* (2006.01)
*H01L 27/00* (2006.01)

(52) U.S. Cl. ...................... 358/487; 358/475; 358/474; 358/1.1; 382/312; 250/208.1

(58) Field of Classification Search ................. 358/1.1, 358/474, 475, 487; 382/312; 250/208.1
See application file for complete search history.

(56) References Cited

U.S. PATENT DOCUMENTS 5,155,596 A * 10/1992 Kurtz et al. ................ 358/214
6,456,748 B1 * 9/2002 Yushiya et al. ............. 382/312

* cited by examiner

*Primary Examiner*—Edward Coles
*Assistant Examiner*—Houshang Safaipour
(74) *Attorney, Agent, or Firm*—Sughrue Mion, PLLC

(57) ABSTRACT

A light source section for emitting light intended to be irradiated onto a photographic film that is serving as an original to be read is formed from a total of five types of LED, namely, the LEDs 72R and 74R for emitting light in the R wavelength region, the LEDs 76G and 78G for emitting light in the G wavelength region, and the LED 80B for emitting light in the B wavelength region arranged in one row for each type of LED and packed densely together on an aluminum substrate. The emission spectrums of each of the LEDs 72R, 74R, 76G, 78G, and 80B are different from each other. The film type is then detected and the turning on and off and the emission intensity of each LED are controlled so that the spectral characteristics of light emitted from the light source section in accordance with an LED emission pattern determined on the basis of the spectral absorption characteristics of the film match the spectral characteristics of reading light suitable for reading the film.

23 Claims, 14 Drawing Sheets

LIGHT SOURCE DEVICE AND DEVICE FOR READING ORIGINAL

BACKGROUND OF THE INVENTION

1. Field of the Invention

The present invention relates to a light source device and a device for reading an original and method for producing light for reading an original. In particular, the present invention relates to a light source device that emits light which is irradiated onto an illuminated body such as an original, a device for reading an original by converting the light that has passed through the original or the light that has been reflected by the original into electrical signals, and a reading method for an original that can be used by the device.

2. Description of the Related Art

Conventionally, a device for reading an original is known having a structure for reading an image (i.e. image data representing density values for each pixel of the image recorded on the original is obtained) in which light emitted from a light source and passed through an original such as a photographic film on which an image has been recorded is photoelectrically converted for each pixel by a reading sensor such as a CCD and signals obtained from the photoelectric conversion are converted into digital data. Halogen lamps have been widely used as the light source in this type of device for reading an original, however, recent years have seen progress in the light intensification of LEDs. As LEDs have the advantages of being less expensive, smaller, and consuming less power than halogen lamps, LEDs have also become common as light sources in devices for reading an original.

It should be noted that a device for reading an original is capable of reading various types of film such as negative film and reversal film, for example; however, as is shown in FIG. 13, the spectral transmission density characteristics (spectral absorption characteristics) of negative films and reversal films are very different and while a peak is generated in a wavelength of approximately 700 nm for the spectral transmission density of C (cyan) coloring material in a negative film, for example, the spectral transmission density peak in a reversal film has a wavelength of approximately 650 nm, which is a wavelength difference of 50 nm. The reason for this is because the spectral transmission density characteristics of coloring materials of negative films are designed based on the spectral sensitivity characteristics of color paper.

Conventional devices for reading an original, however, that use an LED light source are generally structured with one LED for each of the R, G, and B wavelength regions. As an example, as is clear when the emission spectrum of each LED corresponding to each wavelength region shown in FIG. 14A is compared with the example shown in FIG. 14B of the spectral characteristics of the light emitted from a light source section formed from a halogen lamp and R, G, and B filters (these spectral characteristics are adjusted by the filters such that various types of film can be read stably), the wavelengths where the peaks are generated are very different to each other by as much as a half bandwidth (the LED emission spectrum is smaller by a half bandwidth, namely, has a narrower frequency band).

Accordingly, because the wavelengths where peaks are generated are very different and the frequency band is narrower in the spectral characteristics of the light emitted from the light source portion in a conventional device for reading an original that uses an LED as a light source as compared with the spectral absorption characteristics of the coloring material of the film being read, the accuracy with which the film is read is easily affected by differences in the type of coloring material in the film being read, variations in the LED emission spectrum caused by variations in the surrounding temperature, differences in the characteristics of each individual LED, and the like. Consequently, the problem has existed that it has been extremely difficult to always read a film accurately. Note that this problem also arises in the same way when another light emitting element other than an LED is used as a light source (i.e. a light emitting element having a narrow bandwidth emission spectrum e.g. a laser).

Moreover, when an image recorded on film is copied onto a copying material such as photographic paper, if a light emitting element such as that described above is used as the light source, the problem has arisen that there is a lack of consistency in the end product of the image that is copied onto the copying material due to the effects of differences in the type of coloring material in the film, variations in the LED emission spectrum caused by variations in the surrounding temperature, and differences in the characteristics of each individual LED.

SUMMARY OF THE INVENTION

The present invention was conceived in view of the above circumstances and an object of the present invention is to provide a light source device in which the spectral characteristics of the emitted light are capable of being altered.

A further object of the present invention is to provide a device for reading an original and a method for producing light for reading an original in which it is always possible to accurately read an original.

In order to achieve the above objects, a first aspect of the present invention is a light source device used at the time of separating, into N color components, light which is irradiated toward an original and is one of transmitted through and reflected by the original, said light source device comprises a light source section formed from M light emitting elements having different emission spectrums, wherein M>N; and a controller controlling overall spectral characteristics of light emitted from the light source section by controlling at least one of lighting and extinguishing of each of the M light-emitting elements of the light source section, emission intensity of each of the M light-emitting elements of the light source section, and emission time of each of the M light-emitting elements of the light source section.

In the light source device of the first aspect of the present invention, the light which is illuminated onto the original and is transmitted through or reflected by the original is used at the time when light divided into N color components is received. As one aspect of receiving light which has been divided into N color components, for example, when light of respectively different color components among the N color components is received, the light transmitted through the original or reflected by the original is received by the copy material at which the N coloring materials which form colors are provided, such that the image of the original is copied onto the copy material. Further, as another aspect, for example, the light transmitted through the original or the light reflected by the original is received by a reading sensor which is provided with N light-receiving elements having sensitivities with respect to light of respectively different color components among the N color components, such that the image of the original is read.

The light source section includes M light-emitting elements (wherein M>N) having respectively different light-emitting spectra (e.g., having respectively different peak wavelengths of light-emitting spectra). Thus, the overall spectral characteristic of the emitted light of the light source section can be changed. (The overall spectral characteristic is the spectral characteristic corresponding to the cumulative amount of emitted light of each wavelength region of the light emitted from the light source section within a predetermined period of time (e.g., the period of time from the time when at least one of the light-emitting elements begins to be lit to the time when the lighting of all of the light-emitting elements is completed).)

Namely, as the light source section according to the present invention, specifically, it is possible to use a structure in which light emitting elements are provided corresponding to each color component wavelength region, and the light emitting elements corresponding to at least one color component wavelength region comprise a plurality of light emitting elements each having a different emission spectrum. In this case, by either selectively turning on the plurality of light emitting elements corresponding to the same color component wavelength region, or by changing the emission intensity ratios of each of the plurality of light emitting elements, it is possible to change the spectral characteristics of the light emitted from the light source section in at least one color component wavelength region.

Moreover, it is also possible to use a structure in which, for example, light can be emitted in all of the color component wavelength regions by a plurality of light emitting elements whose emission spectrum peak wavelengths are each shifted by a predetermined value. In this case, by either selectively turning on each light emitting element, or by changing the emission intensity ratios of each of the plurality of light emitting elements, it is possible to change the spectral characteristics of light emitted from the light source section to optional characteristics, although this does depend on the interval between the emission spectrum peak wavelengths of each of the light emitting elements.

Note that it is possible to use, for example, narrow bandwidth light emitting elements (examples of which include LEDs and lasers) as the light emitting elements of the light source section according to the present invention. Moreover, it is also possible to use a combination of light emitting elements having different light emitting principles, as described above, among the plurality of light emitting elements.

In the first aspect of the present invention, the controller controls at least one of the lighting and turning off of the respective ones of the M light-emitting elements of the light source section, the light emitting intensity and the light emitting time, so as to control the overall spectral characteristic of the light emitted from the light source section. As a result, even if the desirable spectral characteristics of the light irradiated onto the material change depending on the application of the light source device (for example, in accordance with the type and characteristics of the material which is irradiated with light emitted from the light source device), the controller is able to make the spectral characteristics of the light emitted from the light source device either match or closely approximate desirable spectral characteristics by controlling at least one of whether each light emitting element is illuminated and the emission intensity of each of the plurality of light emitting elements.

Moreover, even if the characteristics of the light emitting elements are different from desired characteristics (for example, if the emission spectrum of the light emitting elements change due to changes in the temperature, or if the emission spectrums of the light emitting elements are different from the desired spectrums due to individual differences in each light emitting element), the controller is able to make the spectral characteristics of the light emitted from the light source device either match or closely approximate desirable spectral characteristics by controlling at least one of whether each light emitting element is illuminated and the emission intensity of each of the plurality of light emitting elements.

It should be noted that it is also possible to employ the light source unit according to the first aspect of the present invention for copying images recorded on an original onto a copying material by causing the light emitted from the light source device to be irradiated onto a copying material after being transmitted through or reflected by the original. In this case, the finishing of the image copied onto the copying material changes depending on the spectral characteristics of the light emitted from the light source device, and desirable spectral characteristics (spectral characteristics for obtaining an excellent finished product when the image recorded on the original is copied onto the copying material) are determined in accordance with the type and characteristics of the original and the copying material.

In contrast to this, because it is normal for the characteristics of originals and copying materials to be roughly divided according to the type thereof, the controller can, for example, determine desirable spectral characteristics based on the type of at least one of the original and the copying material. Consequently, it is possible to obtain an excellent finished product when copying an image recorded on an original onto a copying material as a result of the controller controlling at least one of whether each light emitting element is illuminated and the emission intensity of each of the plurality of light emitting elements of the light source section in accordance with the determined desirable spectral characteristics.

A second aspect of the present invention is a device for reading an original, the device comprises a light source section formed from M light emitting elements each having a different emission spectrum; a sensing apparatus dividing, into N color components wherein N<M, light which has been emitted from the light source section and has been transmitted through or reflected by an original which is being read, the sensing apparatus converting the divisional color components into electric signals; and a controller for controlling overall spectral characteristics of light emitted from the light source section by controlling at least one of lighting and extinguishing of each light emitting element, emission intensity of each light emitting element, and emission time of each light emitting element.

In the second aspect of the present invention, light emitting elements corresponding to each color component wavelength region are provided as the light source section, and it is possible to employ a structure in which the light emitting elements corresponding to the wavelength region of at least one color component are formed from a plurality of light emitting elements each having a different emission spectrum. In this case, as has been described above, the spectral characteristics of the light emitted from the light source section can be changed in the wavelength region of at least one color component.

Moreover, in the second aspect of the present invention, it is also possible to employ a structure in which, for example, light can be emitted in all of the color component wavelength regions by a plurality of light emitting elements whose emission spectrum peak wavelengths are each shifted by a predetermined value. In this case, it is possible to change the spectral characteristics of light emitted from the light source section to optional characteristics even though, as described above, this does depend on the interval between the emission spectrum peak wavelengths of each of the light emitting elements.

Further, in the second aspect of the present invention, there is provided a detecting device. Light, which is emitted from the light source section and which is transmitted through or reflected by the original which is being read, is incident on the detecting device. The detecting device separates the incident light into N color components (wherein N<M), and converts the color components into electric signals. Due to this detecting device, a reading signal expressing the original being read (specifically, the image recorded on the original) is obtained. Spectral characteristics that are desired (i.e. spectral characteristics that will allow the sensing apparatus to read the original with a high degree of accuracy) in the light emitted from the light source section change depending on, for example, the type and characteristics and the like of the original being read.

In contrast, the controller relating to the third aspect of the present invention controls the overall spectral characteristic of the light emitted from the light source section by controlling at least one of the lighting and extinguishing of the respective ones of the M light-emitting elements of the light source section, the intensity of the emitting light, and the light-emitting time. Thus, the overall spectral characteristic of the light emitted from the light source section can be changed in accordance with the desired overall spectral characteristic. Accordingly, in accordance with the third aspect of the present invention, the original which is being read can always be read with high accuracy.

Therefore, it is desirable if the desired spectral characteristics are determined based on the type of the original which is being read. Because the type of original being read can be detected relatively easily, it is possible to easily determine desirable spectral characteristics and it is possible to read originals of different types all with a high degree of accuracy.

The emission spectrum of the light emitting elements also changes due to the temperature depending on the type of light emitting element in the light source section. In this case, it is preferable if at least one of whether each light emitting element is illuminated and the emission intensity of each of the plurality of light emitting elements of the light source section is controlled in accordance with the change in the emission spectrum of the light emitting element that is due to the temperature. Specifically, this can be achieved by measuring in advance the relationship between, for example, changes in temperature and changes in the emission spectrum of the light emitting elements, detecting the temperature change, and controlling at least one of whether each light emitting element is illuminated and the emission intensity of each of the plurality of light emitting elements such that the changes in the emission spectrum caused by the detected change in temperature are corrected. As a result, it is possible to accurately read an original without the reading being affected by changes in the emission spectrums of the light emitting elements caused by changes in the temperature.

Furthermore, as is also clear from FIG. 13 described above, the peak wavelengths of the spectral absorption characteristics (i.e. the characteristics corresponding to C coloring material), in the red (R) color component wavelength region, in particular, differ greatly between negative films and reversal films. Therefore, when both a negative film and a reversal film are read as originals, it is desirable if the light source section is provided with a plurality of light emitting elements each having a different emission spectrum wavelength region serving as light emitting elements corresponding to the red (R) color component wavelength region, and, when the original being read is a reversal film, it is desirable if the controller uses light emitting elements as the light emitting elements corresponding to the red color component wavelength region whose emission spectrum has been shifted further towards the shorter wavelength side than light emitting elements used as the light emitting elements corresponding to the red color component wavelength region when the original being read is a negative film. As a result, it becomes possible to read both negative films and reversal films with a great deal of accuracy regardless of the differences in the peak wavelengths of the spectral absorption characteristics in the red (R) color component wavelength region of negative and reversal films.

Furthermore, although a plurality of light emitting elements such as LEDs and the like having different emission spectrums to each other are available on the market, the brightness of the light emitted by each differs greatly between individual light emitting elements. As an example thereof, when the original being read is a negative film, it is desirable if a light emitting element having an emission spectrum peak wavelength in the vicinity of 550 nm is used as the light emitting element corresponding to the green (G) color component wavelength, however, currently, the brightness of the light emission of an LED having an emission spectrum peak wavelength in the vicinity of 550 nm is no more than approximately one-tenth of the brightness of the light emission of an LED having an emission spectrum peak wavelength in the vicinity of 525 nm.

Therefore, the light source section is provided with a plurality of light emitting elements each having a different emission spectrum as light emitting elements corresponding to the wavelength region of a particular color component, and when the original being read is a particular type, the controller turns on each of the plurality of light emitting elements as light emitting elements which correspond to the wavelength region of the particular color component.

Consequently, if the reading of the particular type of original to be read is performed using as the light emitting element corresponding to the particular color component wavelength region only a single type of light emitting element having an emission spectrum suitable for the reading of the particular type of original to be read from among the plurality of light emitting elements, if the amount of light in the wavelength region of the particular color component from among the light emitted from the light source section is insufficient because the brightness of the emission of the light emitting element is insufficient, by turning on each of the plurality of light emitting elements as the light emitting elements corresponding to the wavelength region of the particular color component, it is possible to prevent the amount of light in the particular color component wavelength frequency from being insufficient and to enable the original being read to be read with a great deal of accuracy.

Moreover, in the format in which respective light emitting elements are provided corresponding to the wavelength regions of each color component of the light source section, if the original being read is a monochrome film, it is preferable if light emitting elements are turned on simultaneously for two or more color component wavelength regions (and more preferably for all color component wavelength regions). Alternatively, it is also possible to turn on only the light emitting element corresponding to a particular single color component wavelength region (for example, a light emitting element of a wavelength region having a high emission brightness: an example of which is the aforementioned LED with the emission spectrum peak wavelength of 525 nm). As a result, the amount of light irradiated onto the monochrome film serving as the original being read is increased enabling the monochrome serving as the original being read to be read in a short time.

Note that, it is also possible to employ a structure comprising a plurality of light source units each emitting light having different spectral characteristics as the light source section according to the second aspect of the present invention. In this case, it is possible to change the spectral characteristics of the light emitted from the light source section as a result of the controller turning on different light source units in accordance with the type of original being read. Consequently, although a variety of light emitting elements are necessary, the control by the controller is simplified.

It is also possible to employ a structure, for example, comprising a single light source unit in which there are provided light emitting elements corresponding to each color component wavelength region, and the light emitting elements corresponding to at least one component color wavelength region are formed from a plurality of light emitting elements each having a different emission spectrum. In this case, although the control by the controller is more complicated than when a plurality of light source units are provided, it is possible to reduce the number of light emitting elements.

It should be noted that when at least one of whether each light emitting element is illuminated and the emission intensity of each of the plurality of light emitting elements of the light source section is controlled in accordance with the desired spectral characteristics of the emitted light that change in accordance with the type and the like of the original being read, and the spectral characteristics of the light emitted from the light source section are changed, it is necessary to compensate in the results obtained by the sensing apparatus for differences in the spectral characteristics in the light emitted from the light source section during the reading when the original is one that has been read using light having differing spectral characteristics.

Therefore, further image processor may be provided for performing image processing on image data obtained by the sensing apparatus under processing conditions that correspond to the control of the light source section by controller. Note that density conversion processing and the like may be cited as an example of such image processing. Because image processing is performed on image data obtained when an original is read under processing conditions that correspond to the control of the light source section, it becomes possible to compensate for differences in the spectral characteristics of the light emitted when the original is read.

A third aspect of the present invention is a method for producing light for reading an original, wherein the light is either transmitted through an original to be read or reflected by the original, and thereafter, the light is separated into N color components, and electrical signals are produced, the method comprises the steps of: forming a light source section from M light emitting elements each having a different emission spectrum, wherein M>N; determining a type of the original, which will be read using emitted light from the light source section; selecting desired overall spectral characteristics for light emitted from the light source section based on the type of the original; and providing overall spectral characteristics for light emitted from the light source section by controlling at least one of whether each of the M light emitting elements is illuminated, emission intensity of each of the M light emitting elements, and emission time of each of the M light emitting elements, in accordance with the selected overall spectral characteristics. Accordingly, in the same way as in the second aspect of the present invention, an original to be read can be read consistently with a great deal of accuracy.

DESCRIPTION OF THE PREFERRED EMBODIMENTS

Examples of the embodiments of the present invention will be described below in detail with reference made to the drawings.

FIRST EMBODIMENT

Figure 1:
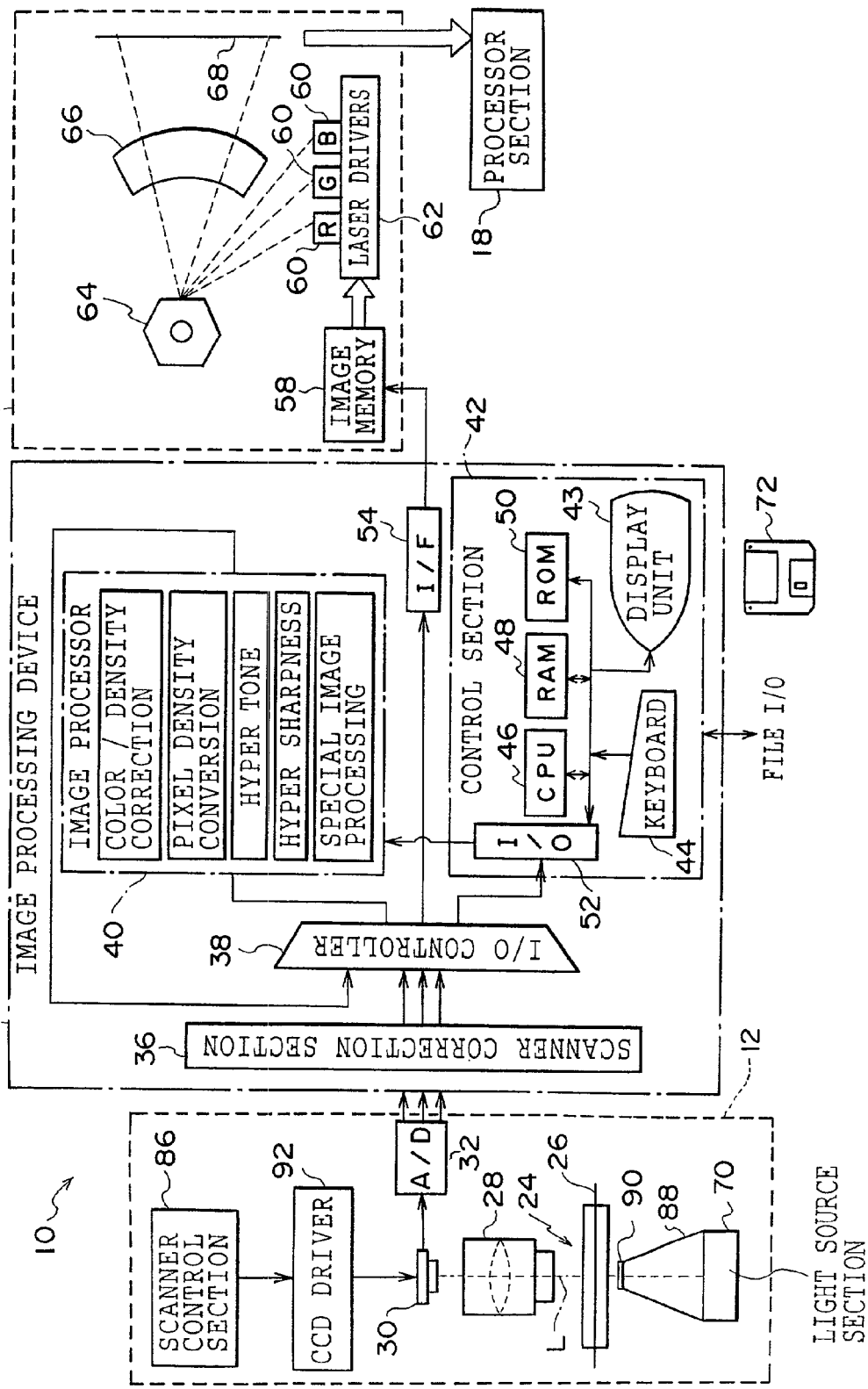
FIG. 1 is a schematic structural view of an image processing system according to an embodiment of the present invention.

FIG. 1 shows an image processing system 10 according to the present embodiment. The image processing system 10 is formed from a film scanner 12 serving as a device for reading an original in which the reading method for an original according to the present invention has been applied, an image processing device 14, and a printer 16 each connected in series.

The film scanner 12 reads a photographic photosensitive material (i.e. the original of the present invention—referred to below simply as a photographic film) such as the photographic film 26 (for example, a negative film or reversal film) (specifically, the film scanner 12 reads film images (i.e. negative or positive images of a photographed object that are visualized by undergoing developing processing) recorded on the photographic film) and outputs image data obtained from the reading.

Figure 2:
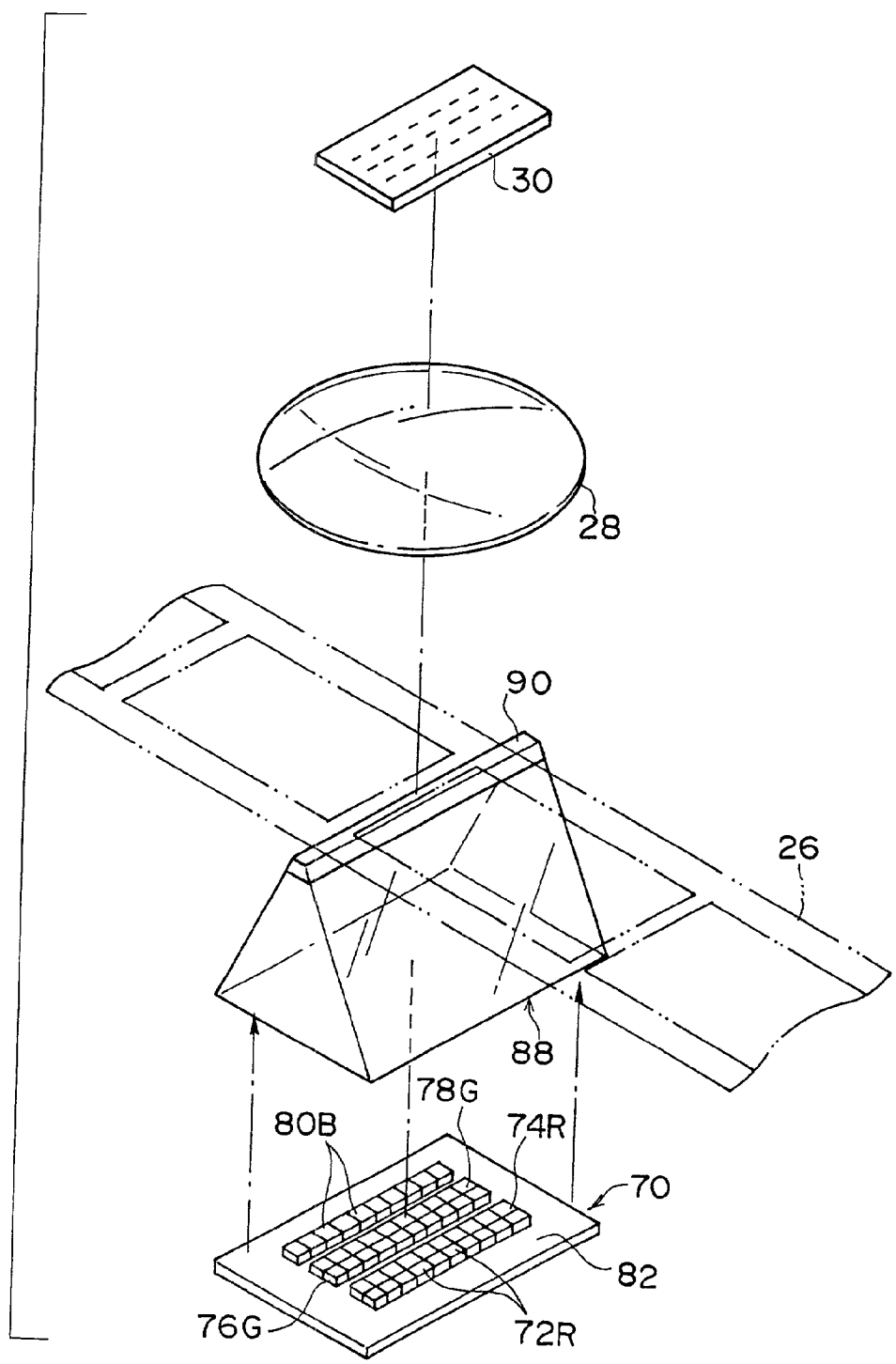
FIG. 2 is a perspective view showing the schematic structure of an optical system of a film scanner.
Figure 3:
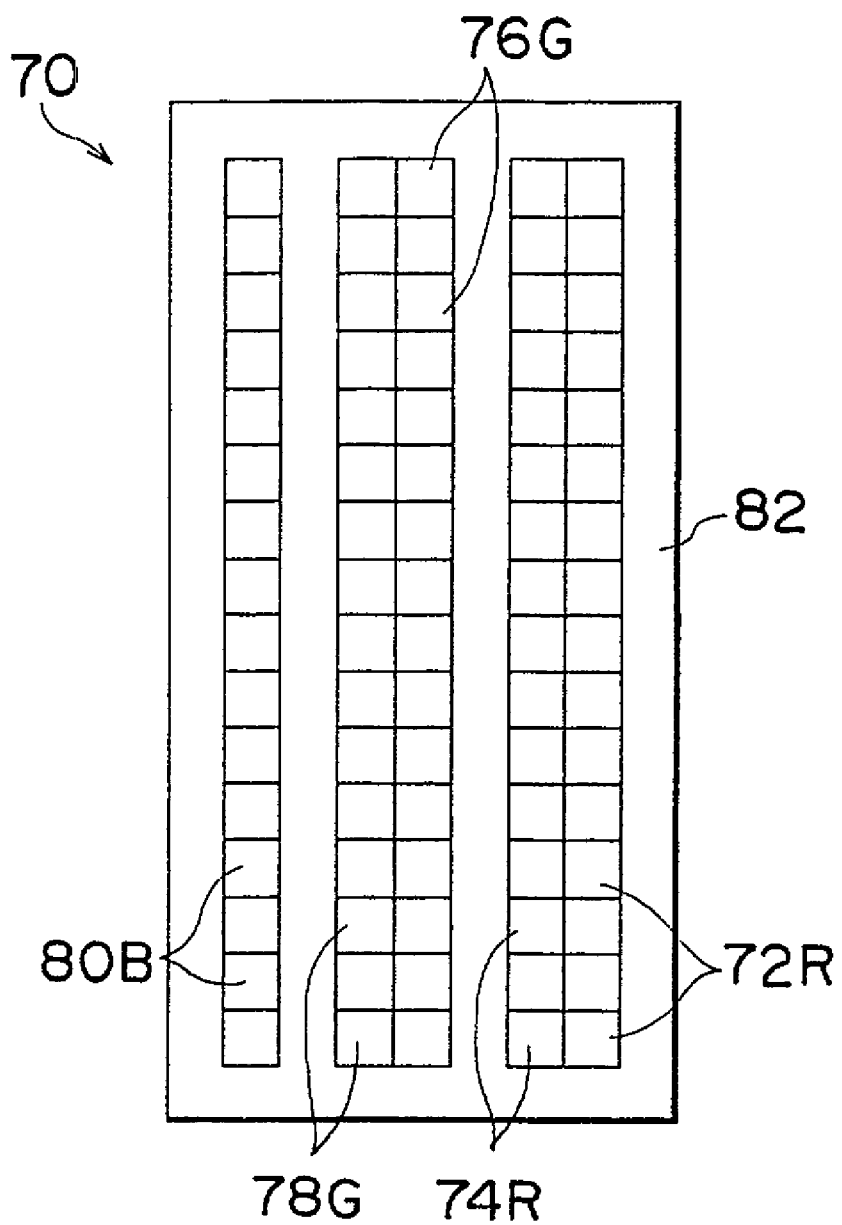
FIG. 3 is a plan view showing the arrangement of LEDs of a light source section according to the first embodiment.

FIG. 2 shows the schematic structure of the optical system of the film scanner 12. The film scanner 12 is provided with a plurality of LED serving as the light emitting elements of the present invention and is also provided with a light source section 70 for emitting the light for irradiating onto the photographic film 26. The light source section 70 according to the first embodiment is provided with a total of five types of LED, namely, the LED 72R and 74R for emitting light in the R wavelength region (i.e. the red color component), the LED 76G and 78G for emitting light in the G wavelength region (i.e. the green color component), and the LED 80B for emitting light in the B wavelength region (i.e. the blue color component). A plurality of LEDs are arranged in one row for each type of LED on an aluminum substrate 82 and are packed densely together (see also FIG. 3).

Figure 4:
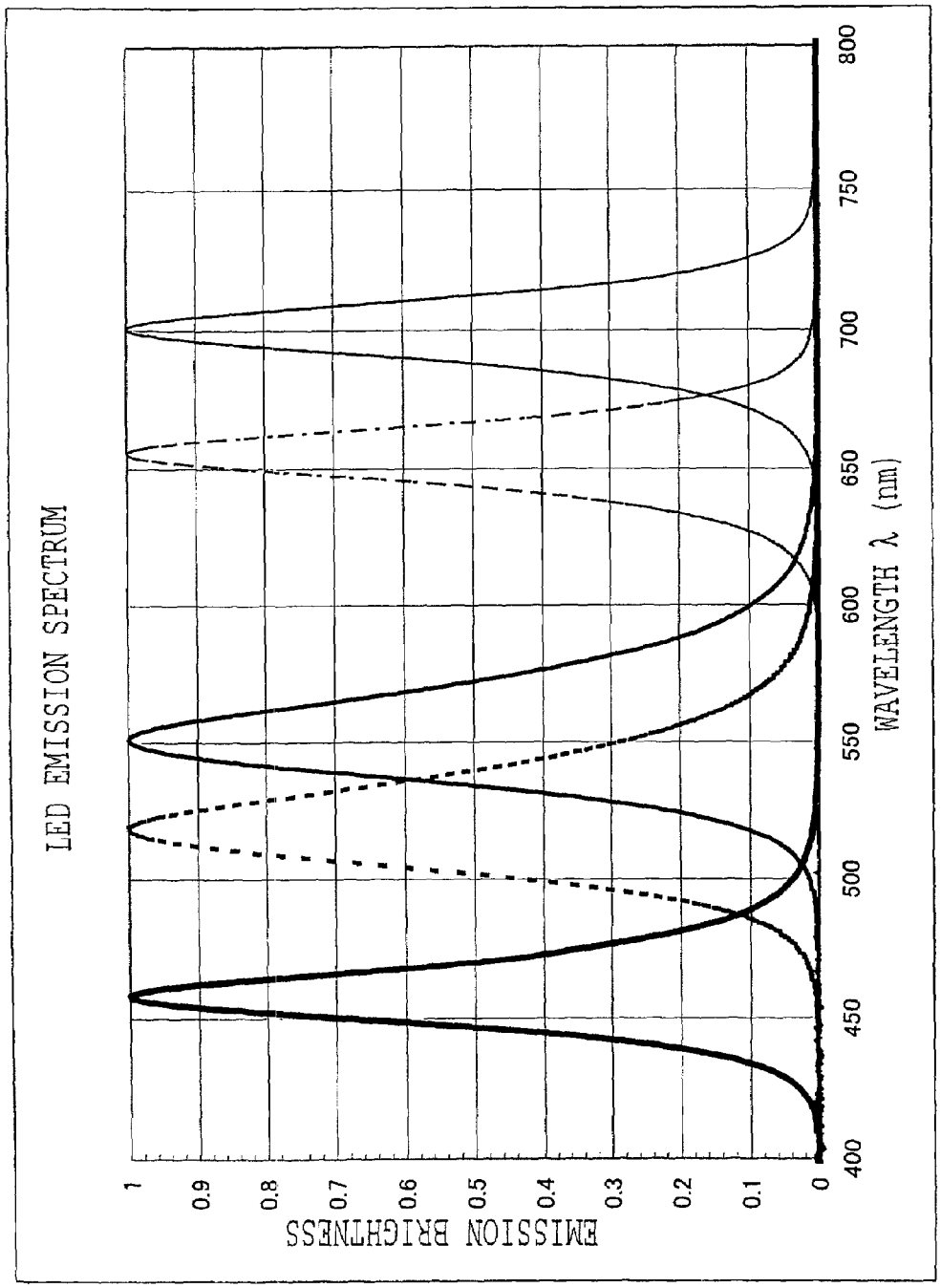
FIG. 4 is a line diagram showing each of the emission spectrums of the various types of LED of the light source section according to the first embodiment.

As is shown in FIG. 4, the five types of LED 72R, 74R, 76G, 78G, and 80B each have different emission spectrums to each other. Namely, the LED 72R has an emission spectrum in which the wavelength peaks in the vicinity of 700 nm corresponding to the peak wavelength of the spectral absorption characteristics of the C (cyan) coloring material of a negative film (see FIG. 13). The LED 74R has an emission spectrum in which the wavelength peaks in the vicinity of 650 nm corresponding to the peak wavelength of the spectral absorption characteristics of the C (cyan) coloring material of a reversal film (see FIG. 13).

Figure 13:
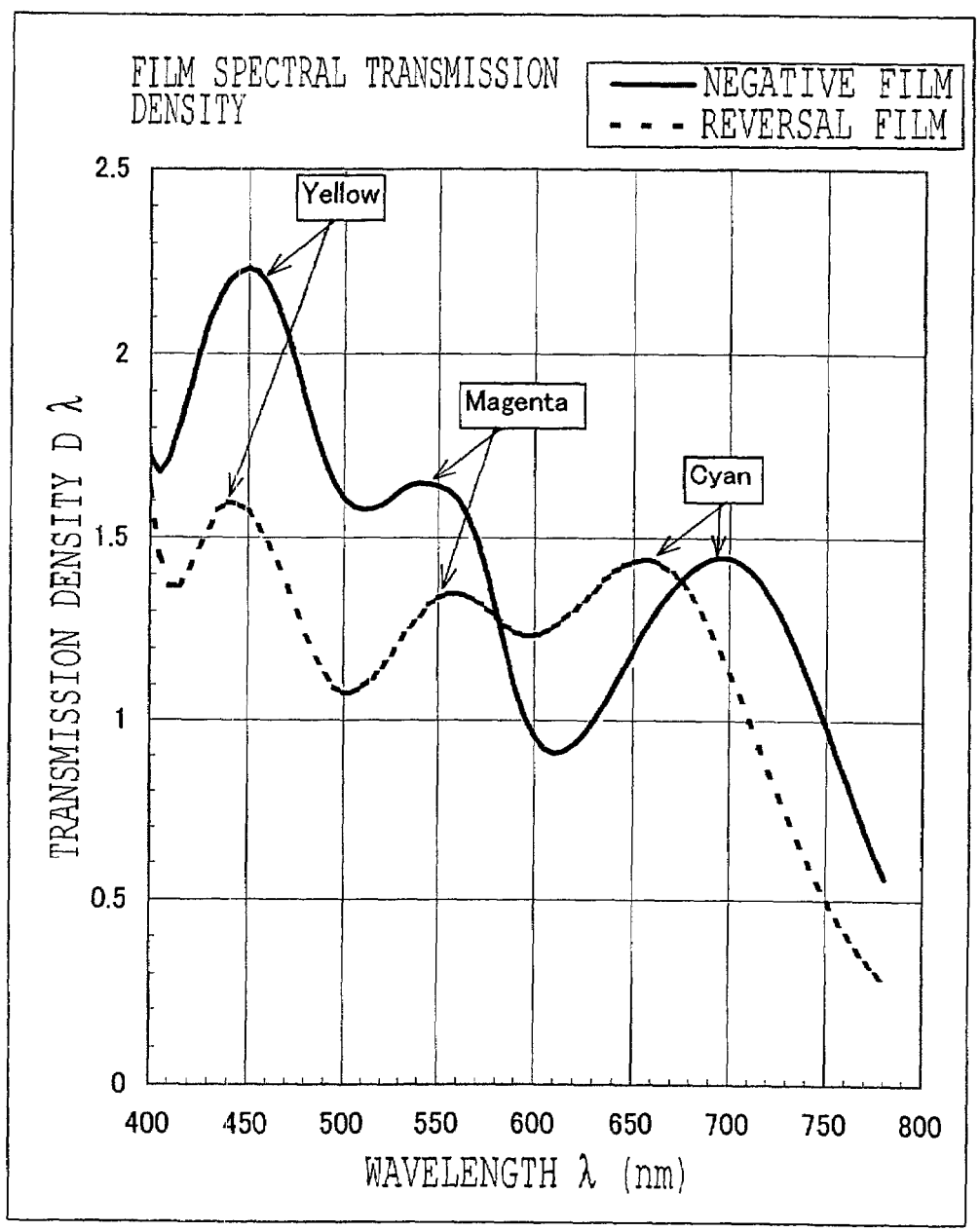
FIG. 13 is a line diagram showing an example of the spectral transmission density characteristics (spectral absorption characteristics) of a negative film and a reversal film.
Figure 14B:
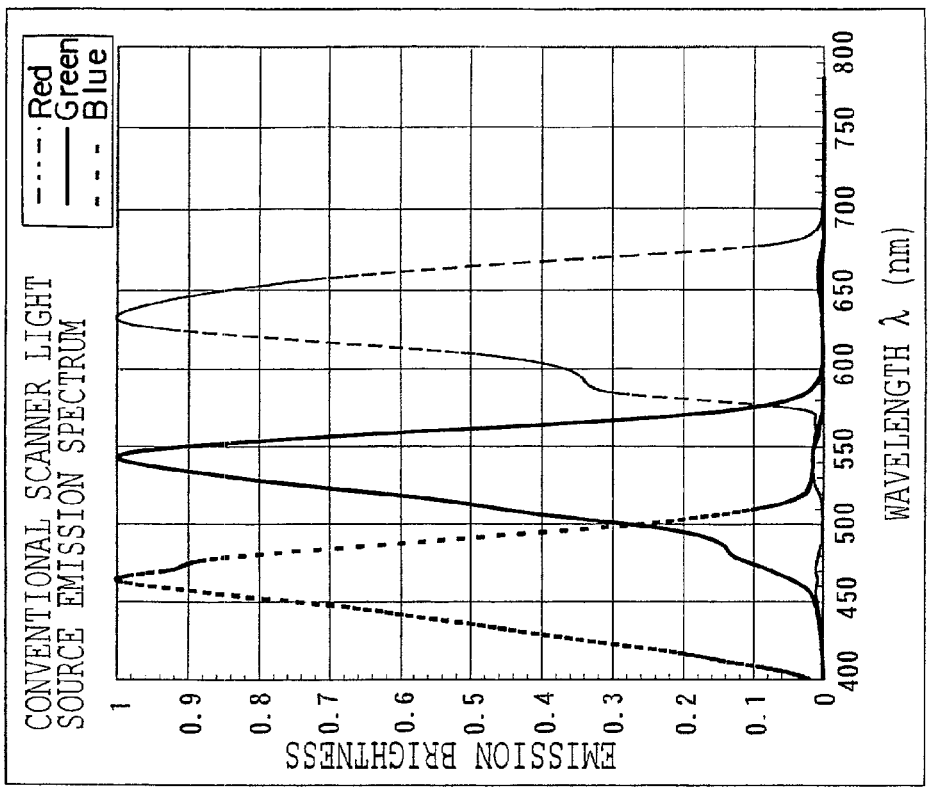
FIG. 14B is a line diagram showing an example of the spectral characteristics of light emitted from a conventional light source section formed from a halogen lamp and R, G, and B filters.
Figure 14A:
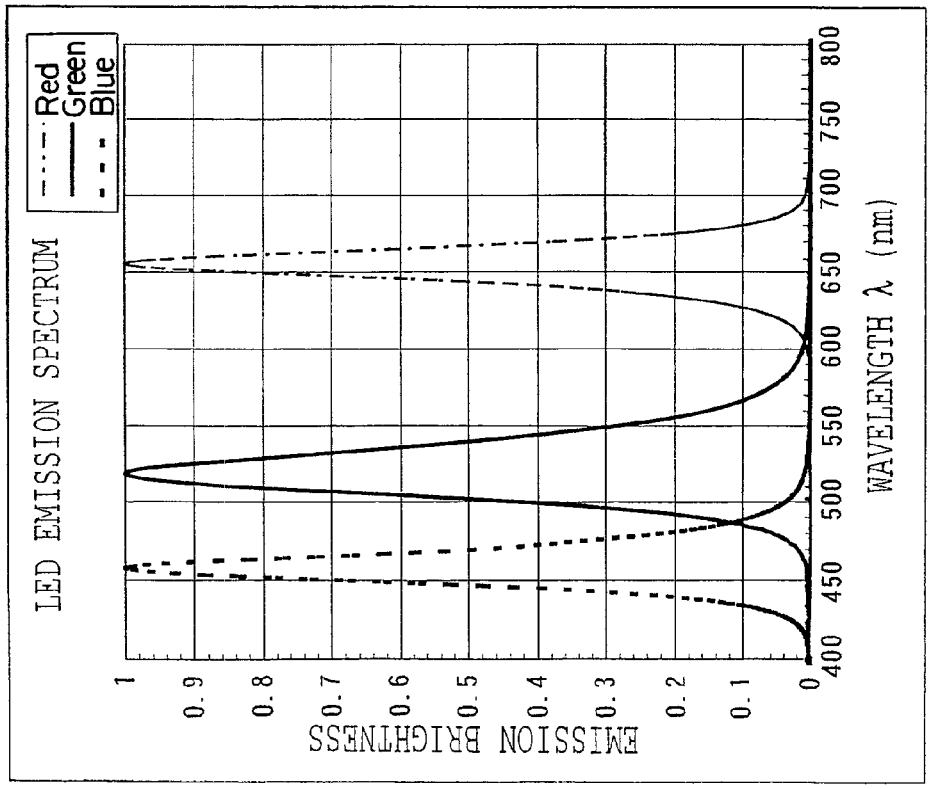
FIG. 14A is a line diagram showing an example of the spectral characteristics of light emitted from a conventional light source section formed from R, G, and B LEDs.

The LED 76G has an emission spectrum in which wavelength peaks in the vicinity of 550 nm corresponding to the peak wavelength of the spectral absorption characteristics of the M (magenta) coloring material of a negative film and a reversal film (see FIG. 13). The LED 78G has an emission spectrum in which the wavelength peaks in the vicinity of 525 nm. In FIG. 4, the brightness of the light emissions from each LED have been standardized with the maximum value of the brightness of the light emission from each LED set at 1, however, in actual fact, the maximum value of the brightness of the light emission from each LED is different. The maximum value of the brightness of the light emission of the LED 76G is approximately one tenth that of the LED 78G. The LED 78G is provided to supplement any insufficiency in the brightness of the light emission from the LED 76G.

The LED 80B has an emission spectrum in which the wavelength peaks in the vicinity of 450 nm corresponding to the peak wavelength of the spectral absorption characteristics of the Y (yellow) coloring material of a negative film and a reversal film (see FIG. 13). Thus, the LEDs 72R, 74R, 76G, 78G, and 80B correspond to the "plurality of light emitting elements each having a different emission spectrum". The Light source section 70 corresponds to the "light source device" and "light source unit".

As is shown in FIG. 2, the substrate 82 of the light source section 70 is arranged such that the direction of the rows of each LED runs in the transverse direction of the photographic film 26 when it is set in the film carrier 24. Each LED is also connected to a scanner control section 86 via an LED driver 84 (see FIG. 5) and the turning on and off of the light source as well as the intensity of the light emission are each controlled by the scanner control section 86. Note that the control of the intensity of the light emission from the LEDs is performed by adjusting the duty ratio of the LED drive current. Moreover, because the substrate 82 on which each of the LEDs is mounted is made from aluminum, the heat generated by the light emission of each LED is almost all conducted by the aluminum plate 82 and discharged.

On the light emission side of the light source section 70 are provided in the following order: an acrylic block 88 formed in a triangular cylinder shape and arranged such that the axial direction thereof runs parallel with the transverse direction of the photographic film 26; and a light diffusion plate 90 attached to the acrylic block 88 on the edge of the acrylic block 88 that faces the photographic film 36. Each LED of the light source section 70 is coated with a protective film (not shown in the drawings) and is fixed to the acrylic block 88 with a transparent adhesive.

The light diffusion plate 90 performs the role of a light conduction member for changing the light that is irradiated from the light source section 70 into diffused light. The overwhelming majority of the light of the different emission spectrums emitted by the plurality of types of LED of the light source section 70 passes through the protective film and the acrylic block 88 and is guided towards the light diffusion plate 90. The light of each LED is uniformly mixed by being further diffused by the light diffusion plate 90 and is irradiated onto the photographic film 26 as reading light in the shape of a slit having a large luminous flux width in the transverse direction of the photographic film 26.

As is shown in FIG. 1, on the opposite side of the film carrier 24 from the light source section 70 are provided along the optical axis of the reading light emitted from the light diffusion plate 90 in the following order a lens 28 and a linear CCD sensor 30 serving as a sensing apparatus. Light that has passed through the photographic film 26 converges on the light receiving surface of the linear CCD sensor 30 via the lens 28.

As is shown in FIG. 2, the linear CCD sensor 30 is provided with three parallel lines with a space between each of sensing sections provided with an electronic shutter mechanism and formed from a plurality of CCD cells arranged in rows along the transverse direction of the photographic film 26. One of either an R, G, or B color decomposition filter is attached to the side of each sensing section struck by the incoming light (forming what is commonly called a 3-line color CCD). Moreover, a transfer section corresponding to each sensing section is provided in the vicinity of each sensing section and the charges that accumulate in each CCD cell in each sensing section are sequentially transferred by the corresponding transfer section.

As is shown in FIG. 1, the film carrier 24 transports the photographic film 26 such that the locations where film images are recorded on the photographic film 26 are sequentially positioned at the reading position (i.e. the position illuminated by reading light). As a result, the film images recorded on the photographic film 26 are sequentially read by the CCD sensor 30 and signals corresponding to the film images are output from the CCD sensor 30. Note that a DX code sensor (not shown in the drawings) for reading the DX code recorded on a photographic film 26 that has been set in the carrier 24 is provided in the film carrier 24. This DX code sensor is connected to the scanner control section 86.

Figure 5:
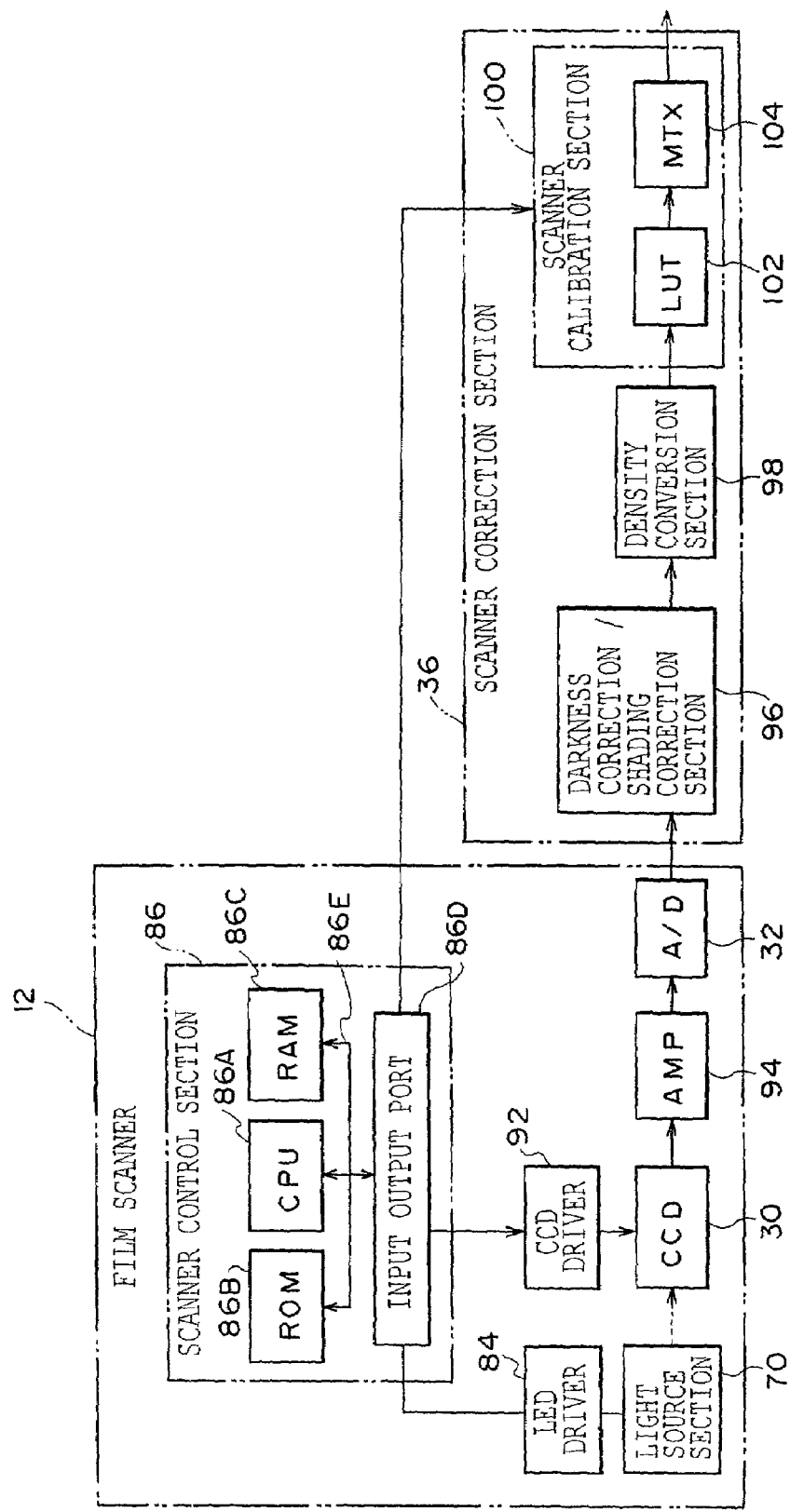
FIG. 5 is a block diagram showing the schematic structure of the control system and signal processing system of a film scanner and a scanner correction section.

As is shown in FIG. 5, the control signal input terminal of the CCD sensor 30 is connected to the scanner control section 86 via a CCD driver 92 and the operation of the CCD sensor 30 is controlled by the scanner control section 86. The scanner control section 86 is provided with a CPU 86A, ROM 86B, RAM 86C, and an input/output port 86D. These are connected to each other via a bus 86E such as a data bus or control bus. The scanner control section 86 corresponds to the controller of the present invention.

Furthermore, the signal output terminal of the CCD sensor 30 is connected to the scanner correction section 36 of the image processing device 14 via an amplifier 94 and an A/D converter 32. Signals output from the CCD sensor 30 are amplified by the amplifier 94, converted into digital image data by the A/D converter 32, and input into the scanner correction section 36.

The scanner correction section 36 of the image processing device 14 is formed with the following connected in the sequence given, namely, a darkness correction/shading correction section 96 for performing darkness correction and shading correction on input image data (i.e. the RGB image data input from the film scanner 12), a density conversion section 98 for logarithmically converting the data output from the correction section 96 into data expressing density values, and a scanner calibration section 100 serving as an image processor.

The scanner calibration section 100 calibrates variations in the data caused by the film scanner 12 and standardizes the data, and is formed from lookup tables 102 and a matrix calculation section 104. The scanner calibration section 100 is connected to the scanner control section 86.

The output terminal of the scanner correction section 36 is connected to an input terminal of an I/O controller 38 and image data that has undergone the various processings in the scanner correction section 36 is input into the I/O controller 38. The input terminal of the I/O controller 38 is also connected to a data output terminal of an image processor 40 and image data that has undergone image processing (described in detail below) is input from the image processor 40.

The input terminal of the I/O controller 38 is also connected to a control section 42. The control section 42 is provided with unillustrated expansion slots and a PC card or IC card capable of being loaded in a digital still camera (these are referred to below as digital camera cards), a driver (not shown in the drawings) for performing the reading and/or writing of data (or a program) on an information storage medium such as a CD-ROM or MO or CD-R or the like, or a communication control device for communicating with another information processing device is connected to this expansion slot. Image data input from the outside via the expansion slot is input into the I/O controller 38.

The output terminal of the I/O controller 38 is connected to both the data input terminal of the image processor 40 and to the control section 42, and is also connected to the printer 16 via an I/F circuit 54. The I/O controller 38 selectively outputs input image data to each of those devices connected to its output terminal.

In the present embodiment, two readings are made at different resolutions in the film scanner 12 of each image recorded on the photographic film 26. In the first reading, which is at a comparatively low resolution (i.e. the prescan), each image reading is performed under reading conditions (i.e. the amount of light in each of the R, G, and B wavelength regions that is illuminated onto the photographic film 26, and the CCD sensor 30 charge accumulation time) set so that saturation of the accumulated charge does not occur in the CCD sensor 30 even when the density of the image is extremely low. The data obtained from the prescan (i.e. the prescan image data) is input into the control section 42 from the I/O controller 38.

The control section 42 is provided with a CPU 46, RAM 48, ROM 50 (for example, ROM whose stored contents are capable of being rewritten), and an input port 52, and these are each connected to each other via a bus. The control section 42 calculates image feature amounts such as image density and the like based on prescan image data input from the I/O controller 38 and sets the reading conditions for when each image is read again in the film scanner 12 at a comparatively high resolution (i.e. the fine scan). The reading conditions that are set are then output to the film scanner 12.

Furthermore, the control section 42 calculates image feature amounts and also extracts the principal image area in each image (for example, an area corresponding to the face of a person—i.e. the facial area) based on the prescan image data and automatically sets by calculation (known as set up calculation) the processing conditions for the respective image processings to be performed on the image data obtained when the film scanner 12 performs the fine scan (i.e. the fine scan image data). The processing conditions that are set are output to the image processor 40. A display unit 43, a keyboard 44, and an unillustrated mouse are also connected to a bus of the control section 42.

Based on the calculated image processing conditions, the control section 42 generates simulation image data by performing the equivalent image processing on the prescan image data as the image processing to be performed in the image processor 40 on the fine scan image data. The simulation image data thus generated is converted into signals for displaying the image on the display unit 43, and a simulation image is displayed on the display unit 43 based on these signals. The image quality and the like of the displayed simulation image may be examined by an operator and information instructing modifications to the processing conditions may be input via the keyboard 44 and mouse as a result of the examination by the operator. The image processing conditions may then be recalculated based on the information input in this way.

The image data input into the I/O controller 38 as a result of the fine scanning of the image in the film scanner 12 (i.e. the fine scan image data) is input into the image processor 40 from the I/O controller 38.

The image processor 40 is provided with image processing circuits for performing various types of image processing such as color and density correction processing including gradation conversion and color conversion, pixel density conversion processing, hyper tone processing to compress the gradation of ultra low frequency brightness components of an image, hyper sharpness processing to enhance sharpness while suppressing graininess, and the like. The image processor 40 performs the various image processings on input image data in accordance with the processing conditions for each image set and forwarded by the control section 42.

When the image data which has undergone image processing in the image processor 40 is to be used for recording an image on photographic printing paper, the image data that has been image processed in the image processor 40 is output from the I/O controller 38 to the printer 16 via an I/F circuit 54 as image data for recording. When image data that has been image processed is to be output to the outside as an image file, the image data is output from the I/0 controller 38 to the control section 42. As a result, in the control section 42, the image data input from the I/O controller 38 for output to the outside is output to the outside (i.e. to the aforementioned driver or communication control device) via an expansion slot as an image file.

The printer 16 is provided with image memory 58, R, G, and B laser light sources 60, and a laser driver 62 for controlling the operation of the laser light sources 60. The image data for recording that has been input from the image processing device 14 is temporarily stored in the image memory 58, read, and then used to modulate the R, G, and B laser light emitted from the laser light sources 60. The laser light emitted from the laser light sources 60 is scanned onto printing paper 68 via a polygon mirror 64 and an fθ lens 66, and an image is thereby recorded by exposure on the printing paper 68. The printing paper 68 on which the image has been exposure recorded is transported to a processor section 18 where it undergoes color developing, bleaching and fixing, washing, and drying processes. As a result of this, the image that was exposure recorded on the printing paper 68 is visualized.

Figure 6:
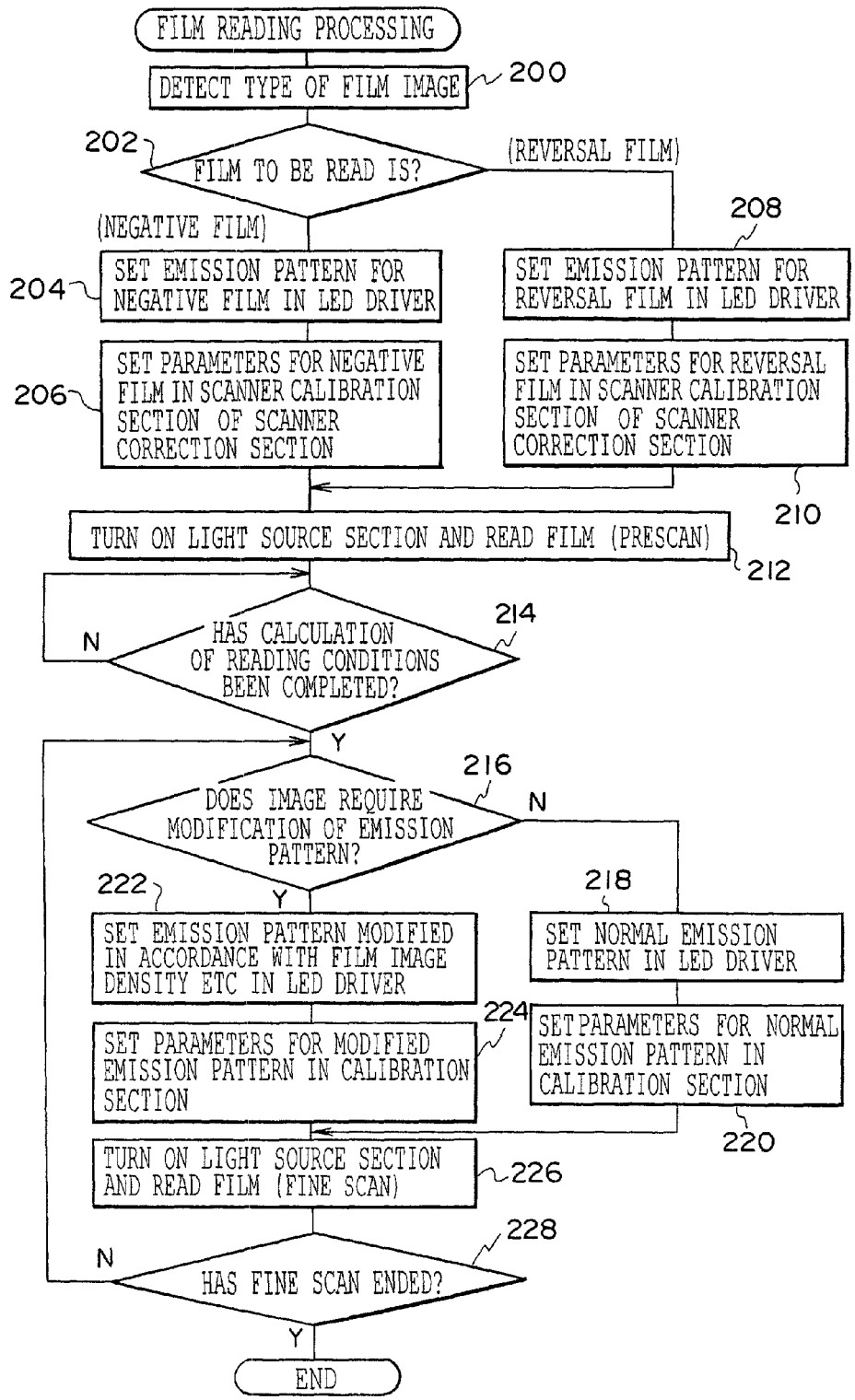
FIG. 6 is a flow chart showing the contents of film reading processing according to the first embodiment.

Next, the film reading process performed by the CPU 86A of the scanner control section 86 when the reading (both prescan and fine scan) of a film image recorded on the photographic film 26 is performed in the film scanner 12 will be described as an operation of the first embodiment with reference made to the flow chart shown in FIG. 6.

In step 200, the DX code recorded on a photographic film 26 (i.e. the film to be read) set in the film carrier 24 is detected by the DX code sensor and the film type is detected for the film to be read by importing and analyzing the DX code detection results. In step 202, a determination is made as to whether the film to be read is a negative film or a reversal film.

The emission patterns (i.e. data determining the emission intensity and the turning on and off of each LED) of each LED of the light source section 70 are stored in the ROM 86B of the scanner control section 86 according to whether the film to be read is a negative film or with whether the film is a reversal film. If it is determined in step 202 that the film to be read is a negative film, the routine proceeds to step 204 and the emission pattern for a negative film is read from the ROM 86B and is set in the LED driver 84.

Note that the emission pattern for a negative film according to the first embodiment is determined based on the general (i.e. average) spectral absorption characteristics for various types of negative film. By causing each LED to emit light in accordance with this emission pattern, the spectral characteristics of the light emitted from the light source section 70 are matched with spectral characteristics appropriate to the reading of a negative film.

As an example of an emission pattern for a negative film, a pattern can be used in which, for the R wavelength region, the LED 72R only of the emission spectrum whose wavelength peak is in the vicinity of 700 nm, which corresponds to the peak wavelength of the spectral absorption characteristics of the C coloring material of a negative film, is caused to emit light at a predetermined emission intensity. In the case of the G wavelength region, the LED 76G of the emission spectrum whose wavelength peak is in the vicinity of 550 nm, which corresponds to the peak wavelength of the spectral absorption characteristics of the M coloring material of a negative film (and for a reversal film), is caused to emit light at a predetermined emission intensity. In addition, the LED 78G which has a high emission efficiency in the emission spectrum whose wavelength peak is in the vicinity of 525 nm is caused to emit light to aid the LED 76G. In the case of the B wavelength region, the LED 80B of the emission spectrum whose wavelength peak is in the vicinity of 450 nm, which corresponds to the peak wavelength of the spectral absorption characteristics of the Y coloring material of a negative film (and for a reversal film), is caused to emit light at a predetermined emission intensity.

Note that, in the first embodiment, the negative film corresponds to the "specific type of reading original".

By setting the above described type of emission pattern in the LED driver 84, during the film reading which is described below, the LED driver 84 controls the turning on and off of each LED of the light source section 86 in accordance with the emission pattern set for the negative film. In accordance with this emission pattern, the LED driver 84 also controls the emission intensity of the LEDs that have been turned on by controlling the duality ratio of the drive current supplied to the LEDs that have been turned on. As a result, light having spectral characteristics appropriate for the reading of a negative film is emitted from the light source section 86 and it becomes possible for the CCD sensor 30 to read a film image recorded on a negative film being read with a great deal of accuracy.

Moreover, in the ROM 86B of the scanner control section 86 are stored both the image processing parameters to be set for the matrix calculation section 104 and the lookup tables 102 of the scanner calibration section 100 when the film being read is a negative film, and also image processing parameters to be set for the matrix calculation section 104 and the lookup tables 102 of the scanner calibration section 100 when the film being read is a negative film is a reversal film. These image processing parameters are determined as is described below.

Namely, when the spectral characteristics of the light emitted from the light source section 70 and irradiated onto the film being read change from S ($\lambda$) to P ($\lambda$), if the transmission density of the film being read is taken as T ($\lambda$), then the reading density before the spectral characteristics change, D1s, and the reading density after the spectral characteristics have changed, D1p, are expressed respectively by the following formulas (i) and (ii).

$$D1s = \Sigma(S \cdot T) \qquad (i)$$

$$D1p = \Sigma(P \cdot T) \qquad (ii)$$

As a result of the change in the spectral characteristics, D1s≠D1p, however, the reading density D1p after the spectral characteristics have changed can be standardized using the following formula (iii) (wherein, D2p is the standardized value for the reading density after the spectral characteristics have changed).

$$D2p = Fp(D1p) \qquad (iii)$$

Accordingly, if the conversion condition Fp in Formula (iii) is determined so as to satisfy "D2p=D1s" and the standardization calculation is performed using the conversion condition Fp, it is possible to calibrate variations in the reading density that arise when the spectral characteristics are changed.

In the present embodiment, by using standard spectral characteristics (for example, the spectral characteristics of light emitted from a lamp source using a halogen lamp) as the spectral characteristics S ($\lambda$), and by using as the spectral characteristics P ($\lambda$) the spectral characteristics when the turning on and off and the emission intensity of each LED is controlled in accordance with the emission pattern for a negative film and the spectral characteristics when the turning on and off and the emission intensity of each LED is controlled in accordance with the emission pattern for a reversal film, and by then determining the conversion conditions Fp for both negative film and reversal film, and by then converting the determined conversion condition Fp into a form in which it can be set in the lookup tables 102 and the matrix conversion section 104, the image processing parameters are determined for both negative films and reversal films.

When the film being read is a negative film, after the processing of step 204 has been performed, the routine proceeds to step 206 where the image processing parameters for a negative film are read from the ROM 86B. After these read image processing parameters have been set in the matrix calculation section 104 and the lookup tables 102 of the scanner calibration section 100, the routine proceeds to step 212. As a result, during the reading of the film image which is described below, the data output from the density conversion section 98 is standardized by the scanner calibration section 100 in accordance with the emission pattern for a negative film (more specifically, the spectral characteristics of light emitted from the light source section 70 when each LED of the light source section 70 is controlled in accordance with an emission pattern for a negative film).

If, however, it is determined in step 202 that the film being read is a reversal film, the routine proceeds to step 208 where the emission pattern for a reversal film is read from the ROM 86B and the emission pattern for a reversal film thus read is set in the LED driver 84.

Note that the emission pattern for a reversal film according to the present first embodiment is also determined on the basis of general (average) spectral absorption characteristics for various types of reversal film. By causing the LEDs to emit light in accordance with this emission pattern, the spectral characteristics of the light emitted from the light source section 70 are matched with spectral characteristics appropriate to the reading of a reversal film.

Note also that, as an example of an emission pattern for a reversal film, a pattern can be used in which, for the R wavelength region, the LED 74R only of an emission spectrum whose wavelength peak is in the vicinity of 650 nm, which corresponds to the peak wavelength of the spectral absorption characteristics of the C coloring material of a reversal film (namely, an emission spectrum whose wavelength region is shifted further towards the short wavelength side than the LED 72R), is caused to emit light at a predetermined emission intensity. In the case of the G and B wavelength regions, the LEDs 76G, 78G, and 80B are caused to emit light in the same way as when the film being read is a negative film.

By setting an emission pattern such as that described above in the LED driver 84, during the film reading which is described below, the LED driver 84 controls the turning on and off of each LED of the light source section 86 in accordance with the emission pattern set for the reversal film. In accordance with this emission pattern, the LED driver 84 also controls the emission intensity of the LEDs that have been turned on by controlling the duality ratio of the drive current supplied to the LEDs that have been turned on. As a result, light having spectral characteristics appropriate for the reading of a reversal film is emitted from the light source section 86 and it becomes possible for the CCD sensor 30 to read a film image recorded on a negative film being read with a great deal of accuracy.

When the film being read is a reversal film, after the processing of step 208 has been performed, the routine proceeds to step 210 where the image processing parameters for a reversal film are read from the ROM 86B. After these read image processing parameters have been set in the matrix calculation section 104 and the lookup tables 102 of the scanner calibration section 100, the routine proceeds to step 212. As a result, during the reading of the film image which is described below, the data output from the density conversion section 98 is standardized by the scanner calibration section 100 in accordance with the emission pattern for a reversal film (more specifically, the spectral characteristics of light emitted from the light source section 70 when each LED of the light source section 70 is controlled in accordance with an emission pattern for a reversal film).

In step 212 a prescan of the film being read is performed. Namely, an instruction is given to the LED driver 84 to turn on the light source section 70 (as a result, the LED driver 84 controls the turning on and off as well as the emission intensity of each LED of the light source section 70 in accordance with the emission pattern previously set, and light having spectral characteristics appropriate for reading the film being read is emitted from the light source section 70). In addition to this, after the charge accumulation time for the CCD sensor 30 has been set in the CCD driver 92 in correspondence with the reading conditions at the time of the prescan, the film being read is transported by the film carrier 24 at a predetermined speed slower than that for the fine scan, which is described below.

Consequently, the light emitted from the light source section 70 and transmitted through the acrylic block 88 and the light diffusion plate 90 is irradiated onto the film being read. Light that passes through the portion of the film being read that is positioned at the reading position sequentially strikes the CCD sensor 30 and the entire surface of the film being read is sequentially passed over the reading position by the film being transported. In addition, the CCD sensor 30 photoelectrically converts the light of each of the R, G, and B wavelength regions from among the light incident thereon and accumulates it as a charge. By repeating this in a predetermined cycle, the entire surface of the film being read is read in sequence.

Note that, in the above described prescan, because the light emitted from the light source section 70 has spectral characteristics appropriate for reading the film being read, it is possible to read the film being read with a great deal of accuracy regardless of whether it is a negative film or a reversal film.

The results of the reading by the CCD sensor 30 (an analog signal representing the accumulated charge amount) are sequentially input via the amplifier 94 and the A/D converter 32 into the scanner correction section 36 of the image processing device 14 as digital image data. In the scanner correction section 36, various processings such as darkness correction, shading correction, conversion into density value data, and the like are performed on the input image data. Thereafter, in the scanner calibration section 100, a standardization calculation is performed in accordance with the image processing parameters set previously. As a result, image data is obtained in which any variations in the reading density that have arisen due to the control of the spectral characteristics of the light emitted from the light source section 70 have been calibrated.

When the prescan of the entire surface of the film being read is performed, the routine waits in the next step 214 until the analysis of each film image and the calculation of the reading conditions for the fine scan are completed in the control section 42 of the image processing device 14 based on the image data output from the scanner correction section 36. When the reading conditions for the fine scan are notified from the image processing device 14, the determination in step 214 is affirmative and the routine proceeds to step 216.

In step 216 and thereafter, a fine scan for sequentially reading each film image recorded on the film being read is performed.

Namely, in step 216, based on the results of the analysis by the control section 42 of the next film image to be read, a determination is made as to whether or not the film image is one that needs to have the emission pattern modified for the fine scan. If the determination in step 216 is negative, the routine proceeds to step 218 where the normal emission pattern for a fine scan is set in the LED driver 84.

Note that it is possible to use the same emission pattern that was used in the prescan as the normal emission pattern for a fine scan. However, because the speed at which the film being read is transported during the fine scan is slower than the speed during the prescan, in the present embodiment, in contrast to the emission pattern used in the prescan, the emission pattern used in the fine scan is one in which the emission intensity of each single LED has been reduced by a fixed ratio by reducing by a fixed ratio the duality ratio of the drive current supplied to each LED to be turned on.

If a normal emission pattern is set in the LED driver 84, then, in the next step 220, the image processing parameters corresponding to the normal light emission pattern are set in the matrix calculation section 104 and the lookup tables 102 of the scanner calibration section 100 and the routine proceeds to step 226.

If, however, for example, the density of the next film image to be read is markedly higher and it is not possible to accurately read the film image simply by adjusting the charge accumulation time of the CCD sensor 30, or if the time needed for the reading is markedly extended, the determination in step 216 is affirmative and the routine proceeds to step 222. After the emission pattern has been modified in accordance with the density of the next film image to be read or the like, the modified emission pattern is set in the LED driver 84. This modification of the emission pattern may be performed as is described below, for example.

If the next film image to be read has an extremely high density, for example, because the brightness of the emission of the LED 76G of the emission spectrum corresponding to the peak of the wavelength of the spectral absorption characteristics of M coloring material of a negative film and reversal film is insufficient, the possibility arises that the accuracy of the reading will be reduced because the amount of light in the G wavelength region during the fine scan will be insufficient. Therefore, when the density of the next film image to be read is extremely high, then, using the G wavelength region as an example, it is preferable if the light emission pattern is modified so that the amount of light in the G wavelength region is ensured by causing the LED 78G to perform the main light emission and, at the same time, the LED 76G is made to emit auxiliary light. Note that the features of film images that need emission pattern modification may be classified in advance and modified emission patterns stored for each category in advance.

When a modified emission pattern has been set in the LED driver 84, then, in the next step 224, image processing parameters corresponding to the modified emission pattern are set in the matrix calculation section 104 and the lookup tables 102 of the scanner calibration section 100. The routine then proceeds to step 226.

In the next step 226, the fine scan of the next film image to be read is performed. Namely, an instruction is given to the LED driver 84 to turn on the light source section 70 (as a result of this, the LED driver 84 controls the turning on and off as well as the emission intensity of each LED of the light source section 70 in accordance with the emission pattern previously set in either step 218 or in step 222). In addition to this, after the charge accumulation time for the CCD sensor 30 has been set in the CCD driver 92 in correspondence with the reading conditions at the time of the fine scan that have been forwarded from the image processing device 14, the film being read is transported by the film carrier 24.

Consequently, the light emitted from the light source section 70 and transmitted through the acrylic block 88 and the light diffusion plate 90 is irradiated onto the film being read. Light that passes through the portion of that area of the film being read where the film image being read is recorded which is positioned at the reading position sequentially strikes the CCD sensor 30 and the entire surface of the recorded area of the film image being read sequentially passes over the reading position as the film being read is transported. As a result, the film image to be read is read.

Note that, in the above described fine scan, because the light emitted from the light source section 70 has spectral characteristics appropriate for reading the film image being read, it is possible to read the film image being read with a great deal of accuracy. Moreover, the image data input into the scanner correction section 36 is standardized by the scanner calibration section 100 of the scanner correction section 36 in accordance with the spectral characteristics of the light emitted from the light source section 70.

In the next step 228, a determination is made as to whether or not a fine scan of all the film images to be read that are recorded on the film being read has been performed. If this determination is negative, the routine returns to step 216 and step 216 and the steps thereafter are repeated. Consequently, a fine scan of all the film images to be read that are recorded on the film being read is sequentially performed and, in the same way as for the prescan, it is possible to read each film image to be read with a great deal of accuracy regardless of whether the film being read is a negative film or a reversal film.

SECOND EMBODIMENT

Figure 7:
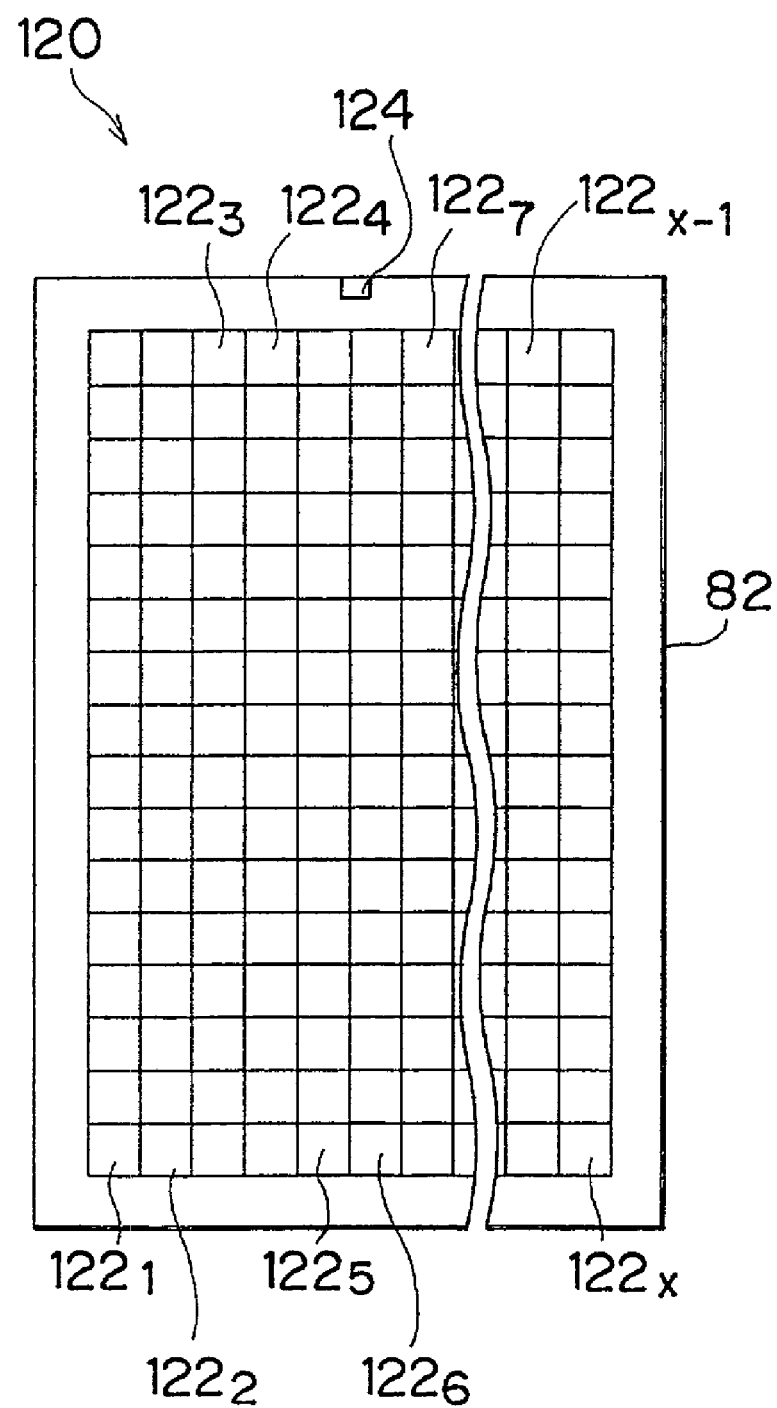
FIG. 7 is a plan view showing the arrangement of LEDs of a light source section according to the second embodiment.

The second embodiment of the present invention will now be described. Note that those sections that are the same as in the first embodiment are given the same symbols and a description thereof is omitted. In the present second embodiment, the light source section 120 shown in FIG. 7 is provided in place of the light source section 70 described in the first embodiment.

Figure 8:
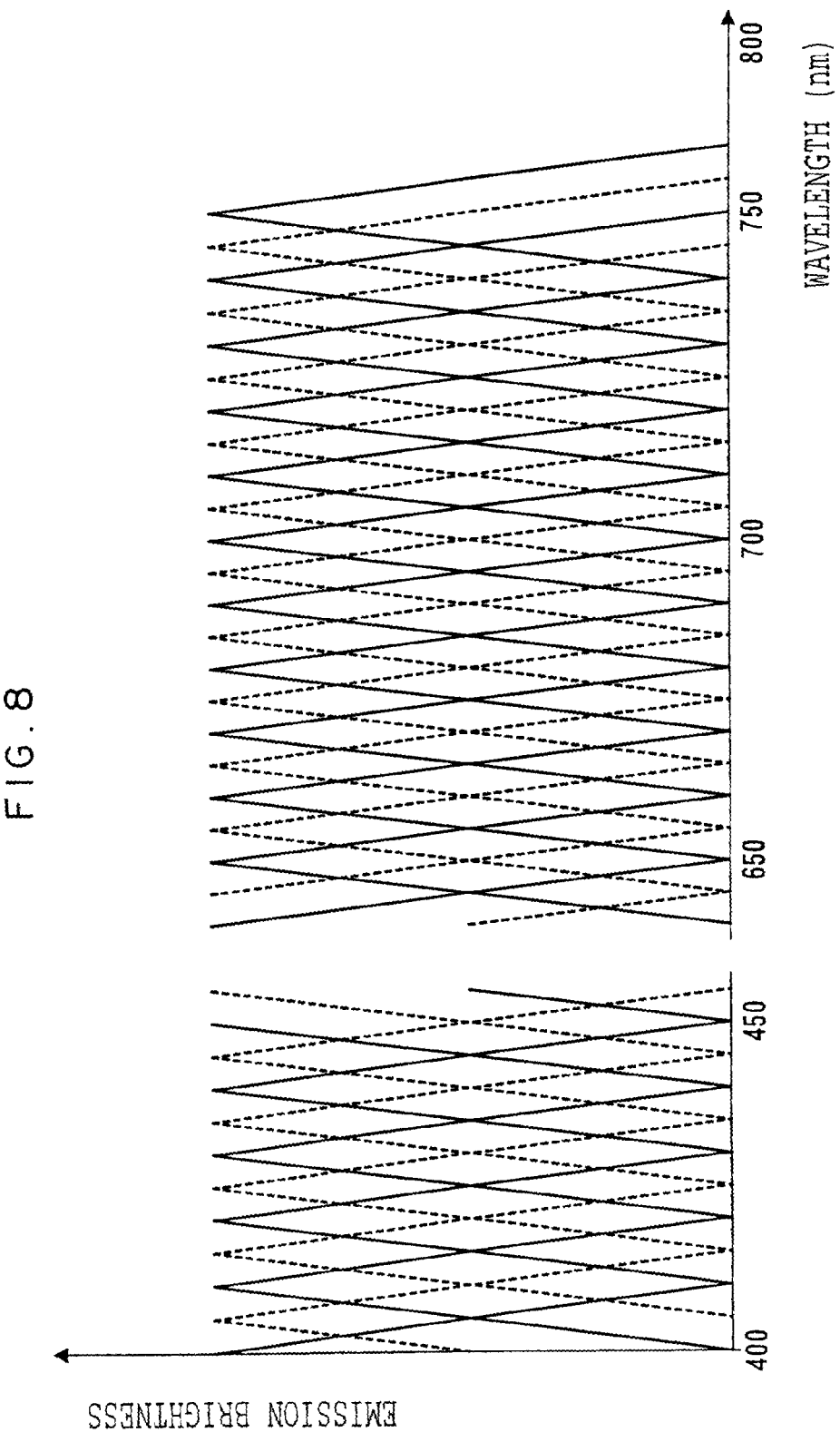
FIG. 8 is a is a line diagram schematically showing each of the emission spectrums of the various types of LED of the light source section according to the second embodiment.

The light source section 120 according to the present embodiment is provided with a plurality of different types of LED $122_1$ to $122_X$ each having a different emission spectrum (specifically, the peak wavelengths of the emission spectrums are different to each other by 5 nm), as is shown schematically in the example in the FIG. 8. A plurality of LEDs are arranged in high density rows on an aluminum substrate 82 with each row comprising one type of LED. The LEDs $122_1$ to $122_X$ correspond to the "plurality of light emitting elements each having a different emission spectrum". The light source section 120 corresponds to the "light source device" and "light source unit".

A temperature sensor 124 for detecting the temperature of the substrate 82 is also provided on the substrate 82. The temperature sensor 124 is connected to the scanner control section 86 and outputs the temperature detection results to the scanner control section 86. Note that the temperature sensor 124 may be positioned so as to detect the temperature of the LED itself, or it may be positioned so as to detect the temperature surrounding the light source section 120.

It should also be noted that not only are the film spectral absorption characteristics very different depending on whether the film is a negative film or a reversal film, but the spectral absorption characteristics of different types of negative film are different from each other and the spectral absorption characteristics of different types of reversal film are different from each other. Therefore, in the present second embodiment, desirable spectral characteristics for the reading light appropriate for reading a film are determined for each type of film on the basis of the spectral absorption characteristics of each type of film. Each group of spectral characteristic data representing the desirable spectral characteristics for the reading light determined for each type of film is stored in advance in the ROM 86B of the scanner control section 86.

Moreover, the LED emission spectrum changes depending on the temperature. As an example, generally, when the temperature rises, the peak wavelength of the LED emission spectrum shifts towards the long wavelength side. In response to this, in the second embodiment, emission spectrum data representing the relationship between the temperature and the emission spectrum for each one of the various types of LED of the light source section 120 is stored in advance in the ROM 86B of the scanner control section 86.

Figure 9:
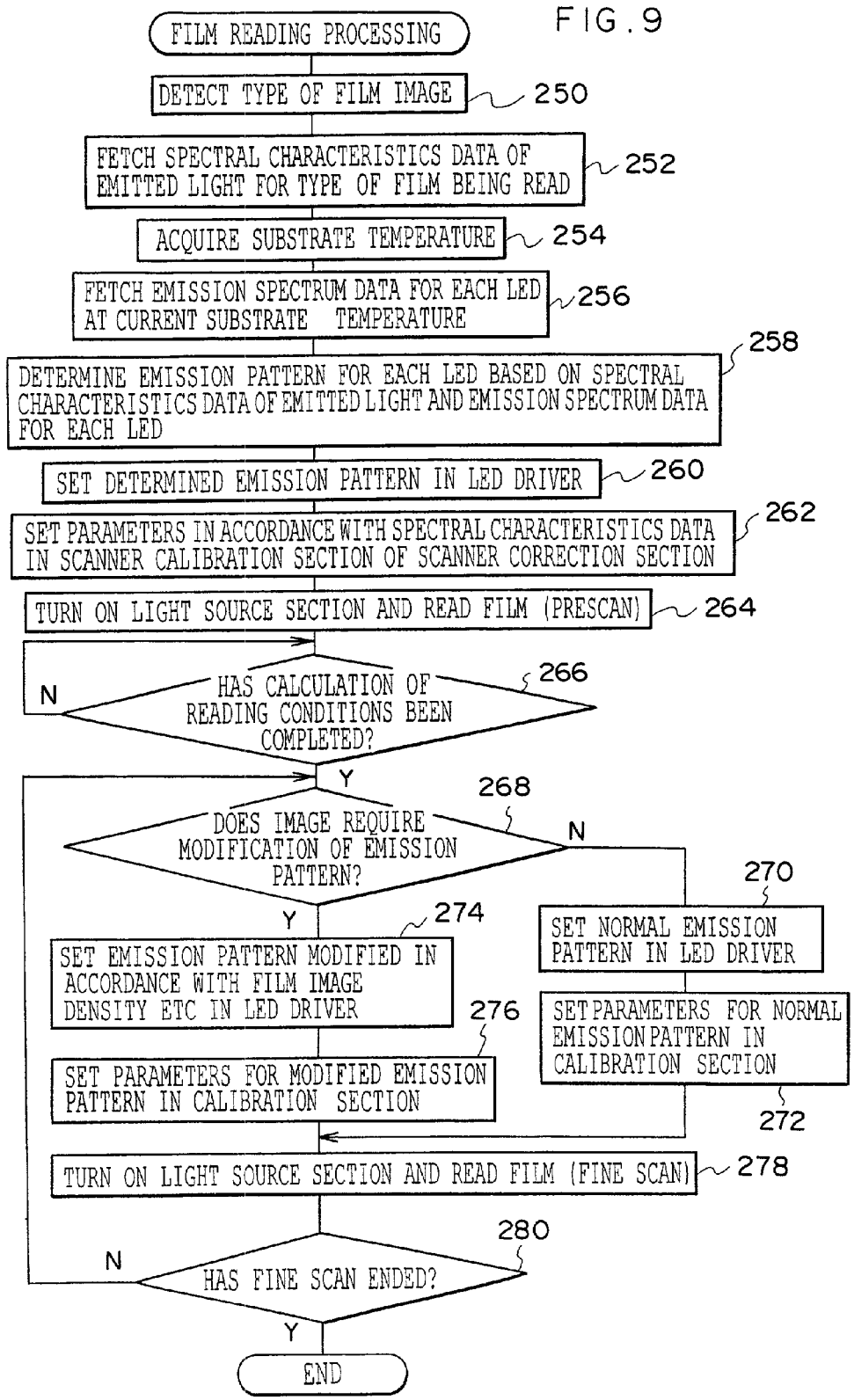
FIG. 9 is a flow chart showing the contents of film reading processing according to the second embodiment.

Next, the film reading processing according to the present second embodiment will be described with reference to the flow chart shown in FIG. 9. In step 250, the type of film that is being read is detected in the same way as in step 200 described in the first embodiment. In the next step 252, spectral characteristic data corresponding to the film type detected in step 250 is fetched from the ROM 86B. In step 254, the value detected for the temperature of the substrate 82 by the temperature sensor 124 is fetched and, in the next step 256, emission spectral data representing the emission spectrum of each LED of the light source section 120 at the current temperature of the substrate 82 represented by the above fetched value is fetched from the ROM 86B.

In the next step 258, based on the spectral characteristic data fetched in step 252 and on the emission spectrum data fetched in step 256, the emission pattern of each LED of the light source section 120 in order to read the film to be read is set. Specifically, this setting of the emission patterns involves combining the current emission spectrums of each LED represented by the emission spectrum data fetched in step 256 and setting the turning on and off as well as the emission intensity of each LED such that light is obtained that has the spectral characteristics represented by the emission characteristic data fetched in step 252.

Consequently, it is possible to obtain emission patterns for controlling each LED such that light having the optimum spectral characteristics (spectral characteristics that correspond to the spectral absorption characteristics of the film being read) for reading the film image to be read is emitted from the light source section 120, regardless of any variations in the emission spectrum of each LED caused by changes in temperature.

In step 260, the emission pattern of each LED set as described above is set in the LED driver 84. In the next step 262, image processing parameters representing the conversion condition Fp (see Formula (i) above) when the spectral characteristic data fetched in step 252 is taken as spectral characteristics P (λ) are set in the matrix calculation section 104 and the lookup tables 102 of the scanner calibration section 100.

In the next step 264, a prescan of the film being read is performed in the same way as in step 212 of the first embodiment. At this time, because light that has appropriate spectral characteristics for reading the film being read is irradiated from the light source section 120 in accordance with the emission patterns set previously in the LED driver 84, it is possible for the CCD sensor 30 to read the film being read with a great degree of accuracy. Moreover, because the image data input into the scanner correction section 36 is standardized in the scanner calibration section 100 in accordance with the spectral characteristics of the light emitted from the light source 120, image data is obtained in which any variations in the reading density that have arisen due to the control of the spectral characteristics of the light emitted from the light source section 120 have been calibrated.

In the next step 266 and thereafter, the routine waits (step 266) until the calculation of the reading conditions for the fine scan is completed in the same way as was described in step 214 of the first embodiment. When the reading conditions are notified, a determination is made as to whether or not the next film image to be read is one requiring the emission pattern to be modified (step 268).

If this determination is negative, the normal emission pattern for a fine scan (for example, an emission pattern in which the emission intensity of each LED in the emission pattern used in the prescan is reduced by a fixed ratio) is set in the LED driver 84 (step 270). Image processing parameters corresponding to this normal emission pattern are then asset in the matrix calculation section 104 and in the lookup tables 102 of the scanner calibration section 100 (step 272).

If, however, the determination in step 268 is affirmative, an emission pattern obtained by modifying the emission pattern used in the prescan in accordance with the density and the like of the next film image to be read is set in the LED driver 84 (step 274), and image processing parameters corresponding to the modified emission pattern are set in the matrix calculation section 104 and in the lookup tables 102 of the scanner calibration section 100 (step 276).

Next, in step 278, in the same way as in step 226 of the first embodiment, a fine scan of the film image being read is performed. At this time, because light having appropriate spectral characteristics for reading (specifically, for fine scanning) the film being read is being emitted from the light source section 120 in accordance with the same emission pattern as used in the prescan (or a modified emission pattern if this has proved necessary), it is possible for the CCD sensor 30 to read the film being read with a great deal of accuracy. Moreover, because the image data is standardized in the scanner calibration section 100, image data is obtained in which any variations in the reading density that have arisen due to the control of the spectral characteristics of the light emitted from the light source section 120 have been calibrated.

Note that the example described above is for when a color film is used for the film to be read, however, the present invention is not limited to this and it is also possible to use a monochrome film for the film to be read. In this case, the reading can be performed by turning on the LEDs simultaneously for the wavelength regions of a plurality of color components (for example, R, G, and B), or the reading can be performed by turning on only the LEDs of a specific single wavelength region having a high level of emission brightness. This latter method is preferable as the amount of light used for the reading can be increased and the reading time shortened.

An example was described above in which the image processing is density conversion (standardization of the read density corresponding to the spectral characteristic of the light emitted from the light source section). However, the present invention is not limited to the same. The aforementioned image processing may be shading correction for correcting dispersion in image data caused by variations in the amount of light emitted from the light source section, aberration of the lens, variation in the sensitivities of the photoelectric conversion cells of the reading sensor (the CCD cells of the CCD sensor 30), or the like. Shading correction is carried out by storing shading correction data for correcting the dispersion in image data, and correcting, by the shading correction data, the image data obtained by reading the image. However, shading correction may also be carried out as follows: plural types of shading correction data corresponding to one of plural types of spectral characteristics (the overall spectral characteristic) of the light emitted from the light source section are stored. From the plural types of shading correction data, the shading correction data corresponding to the spectral characteristic (the overall spectral characteristic) of the emitted light from the light source section is selected. Shading correction is carried out by using the selected shading correction data. As one simple example, at times when a case in which only the light-emitting elements A are lit and a case in which the light-emitting elements A and the light-emitting elements B are lit are possible, shading correction data $SH_A$, which corresponds to the case in which only the light-emitting elements A are lit, and shading correction data $SH_{AB}$, which corresponds to the case in which the light-emitting elements A and the light-emitting elements B are lit, are stored. Shading correction is carried out by using the shading correction data $SH_A$ in the case in which only the light-emitting elements A are lit and by using the shading correction data $SH_{AB}$ corresponding to the case in which the light-emitting elements A and the light-emitting elements B are lit. In this way, shading correction which corresponds to the spectral characteristic (the overall spectral characteristic) of the light emitted from the light source section can be realized.

Figure 10:
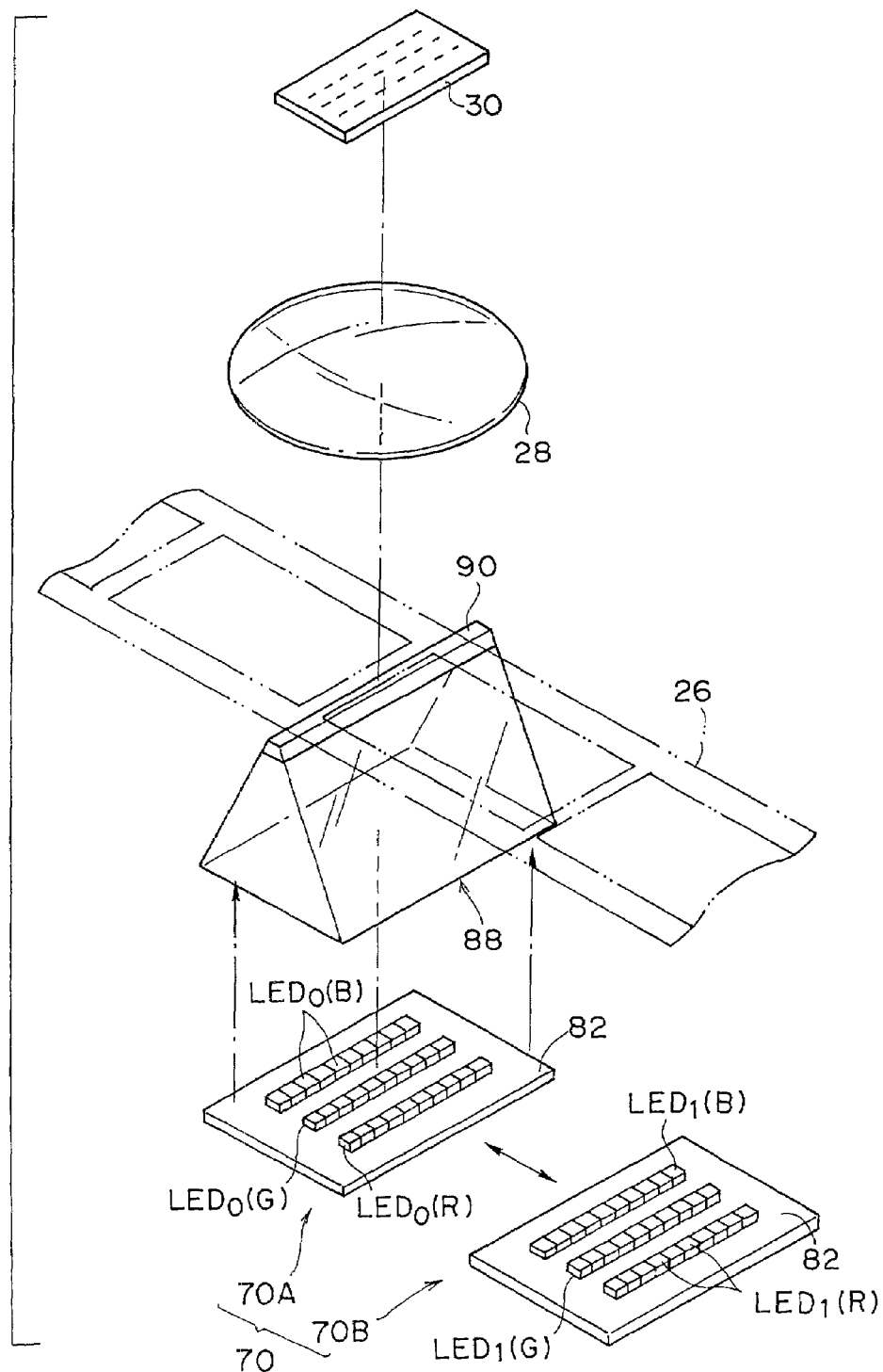
FIG. 10 is a perspective view showing the schematic structure of a light source section provided with a plurality of light source units.

Moreover, in the above description, an example is described of a structure in which the light source section is formed from a single light source unit, however, the present invention is not limited to this and it is also possible to employ a structure provided, as is shown in the example in FIG. 10, with a light source unit 70A comprising three types of LED, namely, a single row each of LED0 (R), LED0 (G), and LED0 (B) arranged on the substrate 82, and a light source unit 70B comprising three types of LED, namely, a single row each of LED1 (R), LED1 (G), and LED1 (B) arranged on the substrate 82. The light source units 70A and 70B are adjusted in advance such that at least the emission spectrums or emission intensity of any of the R, G, and B LEDs are different from the others and that these three LEDs emit light having different spectral characteristics to each other.

In the above structure, control is simplified because the spectral characteristics of the reading light can be changed by switching the light source unit positioned on the optical axis running through the acrylic block 88, the light diffusion plate 90, the photographic film 26, and the lens 28 to the linear CCD sensor 30 (in FIG. 10, the light source 70A is positioned on this optical axis).

Furthermore, in the example in the above description, an LED is used as the light emitting element according to the present invention, however, the present invention is not limited to this and another element such as a laser may be used or a combination of another element such as a laser and LEDs may be used.

Furthermore, in the example in the above description, a linear sensor is used as the sensing apparatus according to the present invention, however, the present invention is not limited to this and an area sensor may also be used.

Figure 11:
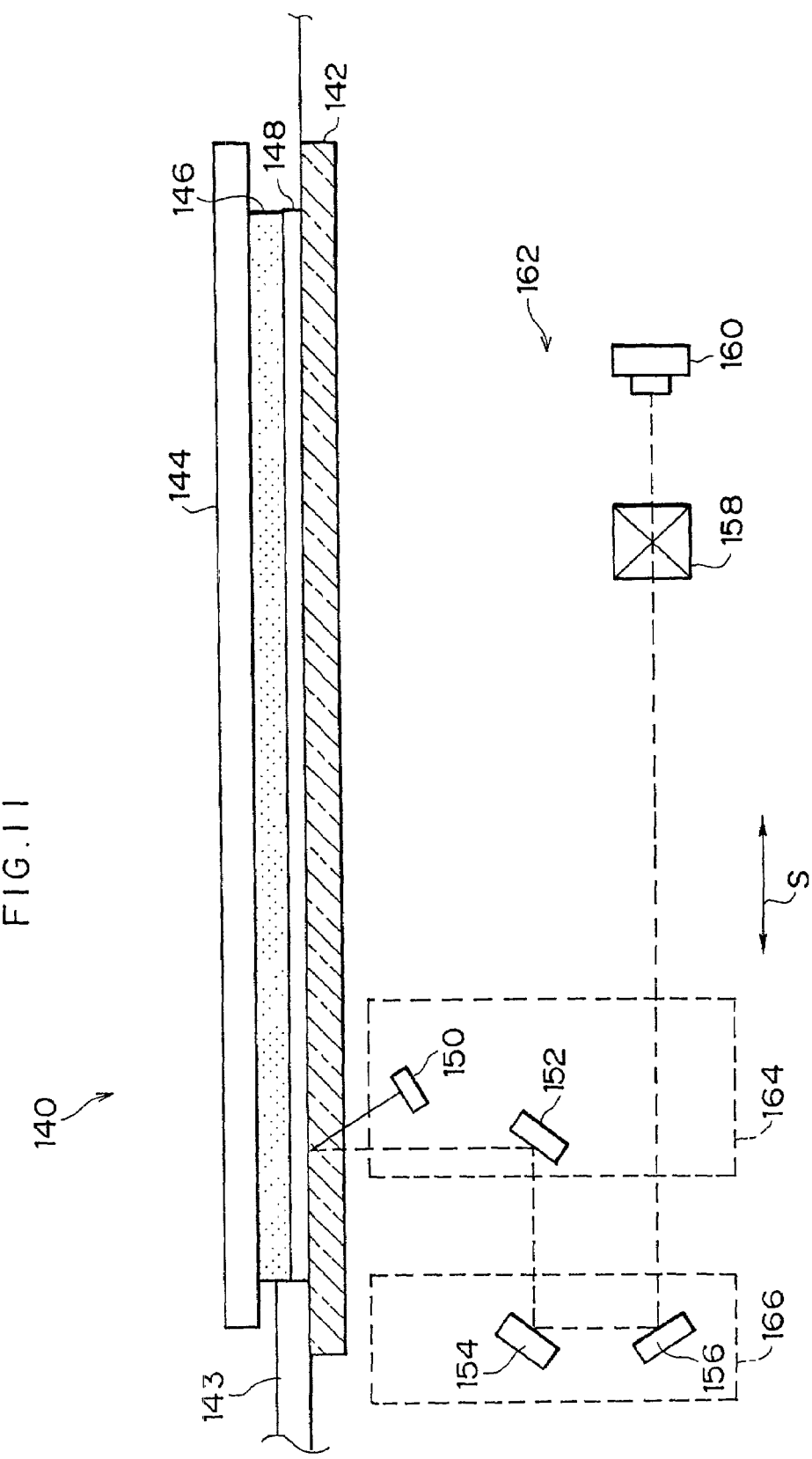
FIG. 11 is a cross sectional view showing the schematic structure of a reflection type of device for reading an original in which the present invention can be applied.

Furthermore, in the example in the above description, a transmission type device for reading an original by photoelectrically converting light transmitted through a photographic film as the original is used as the device for reading an original according to the present invention, however, the present invention is not limited to this. As an example thereof, a reflection type device for reading an original to which the present invention is applied is shown in FIG. 11.

In this device for reading an original 140, an original base is formed from a plate shaped transparent platen glass 142 and guide plates 144 provided at the periphery of the platen glass 142. An original 148 is placed on the platen glass 142 such that the surface on which the image is recorded faces towards the platen glass 142. A platen cover 144 is moved to a position shutting off the original base thereby sandwiching the original 148 between the platen glass 142 and a platen cushion 146 adhered to the rear surface of the platen cover 144. Below the platen glass 142 is positioned a scanning device 162 provided with: a light source section 150 for emitting slit light (i.e. light whose longitudinal direction is the vertical direction on the sheet of paper showing FIG. 11—the same applies in the description below) towards the platen glass 142; an elongated mirror 152 for reflecting light reflected from the platen glass 142 in a substantially horizontal direction; an elongated mirror 154 for reflecting light arriving from the elongated mirror 152 downwards in a substantially vertical direction; and an elongated mirror 156 for reflecting light arriving from the elongated mirror 154 in a substantially horizontal direction; as well as a focusing lens 158 and linear CCD sensor 160 positioned on the light emission side of the elongated mirror 156.

The light source section 150 and the elongated mirror 152 are mounted on a moving section 164, while the elongated mirrors 154 and 156 are mounted on a moving section 166. In order to read the image of an original, the moving section 164 is reciprocally moved at a predetermined speed in the direction shown by the arrow S, and the moving section 166 is moved in the same direction of movement as the moving section 164 at half the predetermined speed of the moving section 164. Consequently, the optical path length from the light source section 150 to the linear CCD sensor 160 is fixed regardless of the position of the moving section 164. It is possible to use a photographic print created by exposing and then developing an image on photographic paper, instant photographs such as photorama and the like, or a printed original and the like as the original to be read by the device 140, however, the spectral absorption characteristics of each of these are different. Therefore, the light source section 150 of the device 140 is formed in the same way as the light source section 70 according to the first embodiment and the light source section 120 according to the second embodiment enabling the spectral characteristics of the light emitted from the light source section 150 to be changed in accordance with the type and the like of the original being read. As a result, it is possible to read a variety of types of originals being read with a great deal of accuracy.

Figure 12:
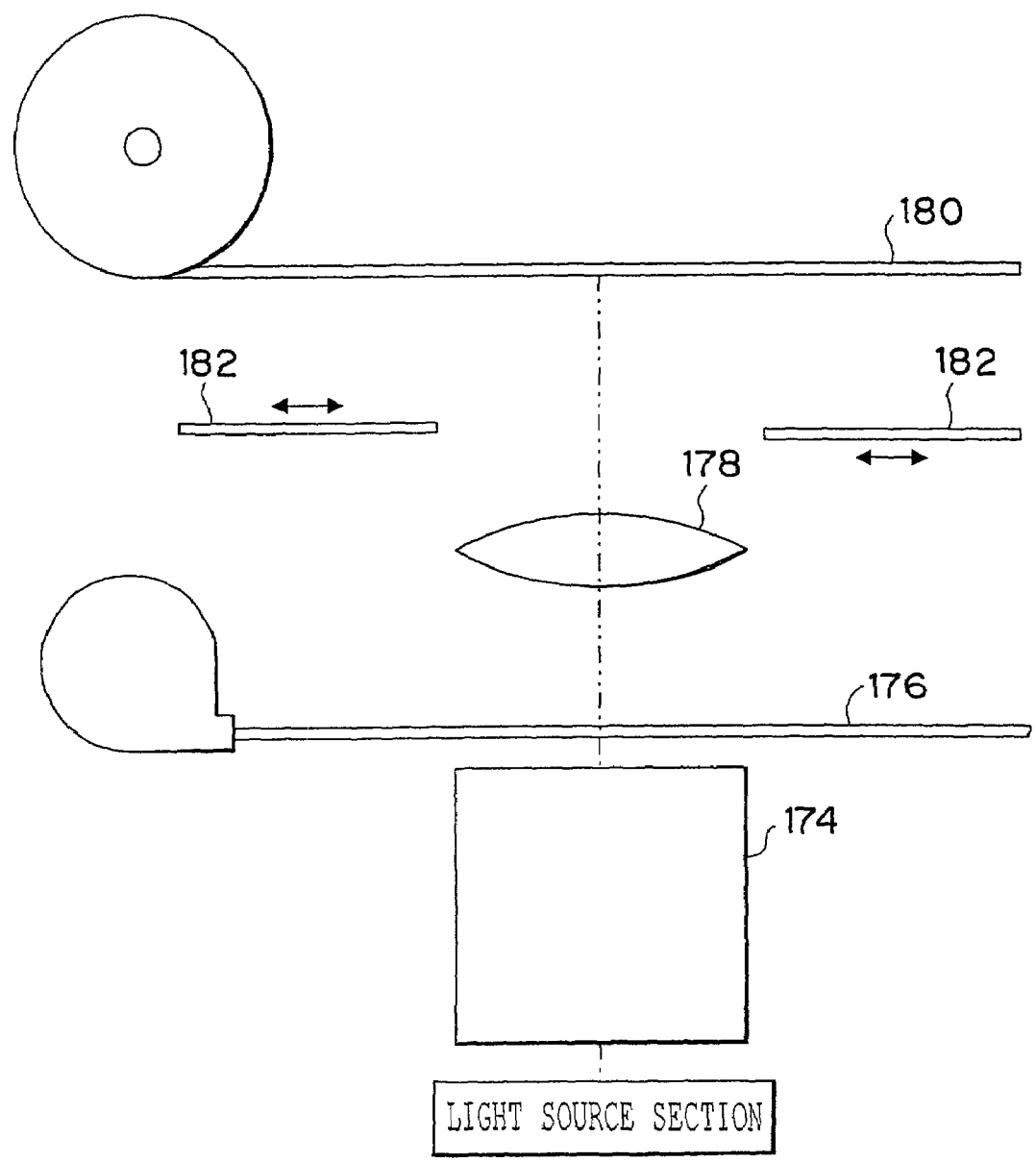
FIG. 12 is a schematic structural diagram of a photographic printing device in which the present invention can be applied.

Furthermore, in the above description, the light source device according to the present invention was used as a light source for reading a film as an original, however, the present invention is not limited to this and the light source device according to the present invention may also be used as a light source for a photographic printing device for exposing images recorded on a photographic film onto photographic paper, or as a light source for a copying device for copying images recorded on a reflection original onto a copying material such as normal paper via an electrophotographic process. An example thereof is the photographic printing device 170, in which the present invention has been applied, shown in FIG. 12.

The photographic printing device 170 is structured such that light emitted from a light source section 172 is diffused by a light diffusion box 174 and irradiated onto a photographic film 176. The light that passes through the photographic film is focused onto photographic paper 180 by a lens 178, thereby exposure recording film images recorded on the photographic film 176 on the photographic paper 180. Note that a black shutter 182 is provided between the lens 178 and the photographic paper 180. As was described in the second embodiment, the spectral absorption characteristics of the photographic film 176 differ depending on the type of photographic film. Therefore, the light source section 172 of the photographic printing device 170 is formed with the same structure as the light source section 70 according to the first embodiment or the light source section 120 according to the second embodiment allowing the spectral characteristics of the light emitted from the light source section 172 to be changed in accordance with the type of photographic film 176 set in the photographic printing device 170. As a result, it is possible to record by exposure film images recorded on different types of photographic film 176 (i.e. on films having different spectral absorption characteristics) onto photographic paper 180 with excellent final results.

Moreover, because there are cases in which the photographic paper 180 set in the photographic printing device 176 is not always the same type of photographic paper and different types of photographic paper are sometimes used, the spectral characteristics of the light emitted from the light source section 172 may be further altered in accordance with the type (spectral absorption characteristics) of the photographic paper 180 set in the photographic printing device 176.

Furthermore, the light source section 120 according to the second embodiment is not limited to being used for reading a film. For example, the light source section 120 may also be used for measuring the spectral absorption characteristics of a film whose spectral absorption characteristics are unknown by turning on each of the various types of LED $122_1$ to $122_X$ of the light source section 120 in sequence so that they irradiate light onto the film in sequence and then sequentially measuring the amount of light passing through the film using a sensor or the like.

Further, a case is described above in which, by controlling the lighting and extinguishing of the respective ones of the plural types of light-emitting elements (LEDs) and by controlling the light-emitting intensity, the spectral characteristic of the light emitted from the light source portion is controlled (the overall spectral characteristic of the emitted light is varied in accordance with the changes in the spectral characteristic of the emitted light). However, the present invention is not limited to the same, and the light-emitting time period of each of the types of light-emitting elements may be controlled. As one example, given that the spectral characteristic of the light emitted from the light-emitting elements is $P_A(\lambda)$ and the spectral characteristic of the light emitted from the light-emitted elements B is $P_B(\lambda)$, the cumulative emitted light amount $LP_A$ when only the light-emitting elements A are emitted for the time $\tau_A$ and the cumulative emitted light amount $LP_{AB}$ when the light-emitting element A are lit for the time $\tau_A$ and the light-emitting elements are lit for the time $\tau_B$ (wherein $\tau_B > \tau_A$ are obtained by the following formulae.

$$LP_A = \sum_{t=0}^{\tau_A} P_A$$

$$LP_{AB} = \sum_{t=0}^{\tau_A} (P_A + P_B) + \sum_{t=\tau_A}^{\tau_B} P_B$$

Accordingly, the overall spectral characteristic $G_{AB}$ at the time when the light-emitting elements A are lit for the time $\tau_A$ and the light-emitting elements B are lit for the time $\tau_B$ is $G_{AB} = P_A(\lambda) + (\tau_A/\tau_B) \times P_B(\lambda)$. (Note that the overall spectral characteristic $G_A$ at the time when only the light-emitting elements A are lit coincides with the spectral characteristic $P_A(\lambda)$ of the light-emitting elements A, i.e., $G_A = P_A(\lambda)$.) An overall spectral characteristic can be obtained which is equal to the lighting, for the time $\tau_B$, of virtual light-emitting elements whose spectral characteristic of the emitted light coincides with the overall spectral characteristic $G_{AB}$. In a case in which the light-emitting times of each of the plural types of light-emitting elements is controlled, although the spectral characteristic itself of the light emitted from the light source section does not vary, the overall spectral characteristic of the light emitted from the light source section can be controlled to the desired characteristic.

Further, in the above description, the charge accumulating time of the CCD sensor 30 at the time of fine scanning is determined in accordance with the density of the film image which is being read which is sensed by the prescanning. However, the charge accumulating time of the CCD sensor 30 can be determined in consideration of the spectral characteristic (the overall spectral characteristic) of the emitted light from the light source section. Specifically, given that the aforementioned overall spectral characteristic G is a reference light amount W0, the reference charge accumulating time at the reference light amount W0 (the maximum time at which saturation of the charge accumulating time does not occur at the CCD sensor 30) is T0, and the optimal light amount determined from the density of the film image which is being read is W, the optimal charge accumulating time T of the image which is being read is:

$T = W/W0 \times T0.$ (With regard to the reference light amount W0, for example, the reference light amount $W0_A$ at the time that only the light-emitting elements A are lit is $W0_A = P_A(\lambda)$, and the reference light amount $W0_{AB}$ at the time when the light-emitting elements are lit for the time $\tau_A$ and the light-emitting elements B are lit for the time $\tau_B$ is $W0_{AB} = P_A(\lambda) + (\tau_A/\tau_B) \times P_B(\lambda)$.) In this way, an optimal charge accumulating time for the CCD sensor 30, which takes into consideration the spectral characteristic (the optimal spectral characteristic) of the emitted light from the light source section, can be obtained. Not only at the time of fine scanning, but at the time of prescanning as well, the charge accumulating time can be determined by taking the spectral characteristic (the overall spectral characteristic) of the emitted light from the light source section into account.

What is claimed is:

1. A light source device used at the time of separating, into N color components, light which is irradiated toward an original and is one of transmitted through and reflected by the original, said light source device comprising:

a light source section formed from M light emitting elements having different emission spectrums, wherein M>N; and a controller controlling overall spectral characteristics of light emitted from the light source section by controlling at least one of lighting and extinguishing of each of the M light-emitting elements of the light source section, emission intensity of each of the M light-emitting elements of the light source section, and emission time of each of the M light-emitting elements of the light source section.

2. The light source device according to claim 1, wherein light emitted from the light source section is irradiated onto a recording material after the light has been either transmitted through an original or reflected by an original, and the controller determines desired overall spectral characteristics on the basis of at least one of a type of spectral transmission density characteristics of the original and a type of spectral sensitivity characteristics of the recording material, and controls at least one of lighting and extinguishing of each of the M light-emitting elements of the light source section, emission intensity of each of the M light-emitting elements of the light source section, and emission time of each of the M light-emitting elements of the light source section, such that the overall spectral characteristics of the light emitted from the light source section coincide with the determined desired overall spectral characteristics.

3. The light source device according to claim 2, wherein the controller determines the desired overall spectral characteristics for the light emitted from the light source section, and when the original is a specific type, the controller selectively illuminates light emitting elements corresponding to a specific color component wavelength region according to the desired overall spectral characteristics.

4. The light source device according to claim 2, wherein the controller determines the desired overall spectral characteristics for light emitted from the light source section, and when the original is a monochrome film type, the controller either illuminates light emitting elements of at least two different color component wavelength regions, or illuminates light emitting elements of only a specific single color component wavelength region.

5. The light source device according to claim 1, wherein light emitting elements are provided in the light source section corresponding to each color component wavelength region, and light emitting elements corresponding to at least one color component wavelength region are formed from a plurality of light emitting elements each having a different emission spectrum.

6. The light source device according to claim 1, wherein the controller controls at least one of whether each light emitting element is illuminated, and light intensity of each light emitting element, in the plurality of light emitting elements of the light source section, in accordance with changes due to temperature in emission spectrums of the light emitting elements.

7. The light source device according to claim 1, wherein light emitted from the light source section is provided with a plurality of light source units, each unit of which emits light having different spectral characteristics, and the controller illuminates different light source units in accordance with a type of the original.

8. The light source device according to claim 1, wherein light emitting elements are provided in the light source section corresponding to each color component wavelength region and light emitting elements corresponding to at least one color component wavelength region are provided with a single light source unit formed from a plurality of light emitting elements each having a different emission spectrum.

9. A device for reading an original, the device comprising:
a light source section formed from M light emitting elements each having a different emission spectrum;
a sensing apparatus dividing, into N color components wherein N<M, light which has been emitted from the light source section and has been transmitted through or reflected by an original which is being read, the sensing apparatus converting the divisional color components into electric signals; and
a controller for controlling overall spectral characteristics of light emitted from the light source section by controlling at least one of lighting and extinguishing of each light emitting element, emission intensity of each light emitting element, and emission time of each light emitting element.

10. The device according to claim 9, wherein light emitting elements are provided in the light source section corresponding to each color component wavelength region, and light emitting elements corresponding to at least one color component wavelength region are formed from a plurality of light emitting elements each having a different emission spectrum.

11. The device according to claim 9, wherein the controller determines desirable spectral characteristics of light emitted from the light source section based on a type of original to be read, and the controller controls at least one of lighting and extinguishing of each of the M light-emitting elements of the light source section, emission intensity of each of the M light-emitting elements of the light source section, and emission time of each of the M light-emitting elements of the light source section such that the overall spectral characteristics of the light emitted from the light source section coincide with the determined desired overall spectral characteristics.

12. The device according to claim 9, wherein the controller controls at least one of whether each light emitting element is illuminated, light intensity of each light emitting element, and emission time of each light emitting element in the plurality of light emitting elements of the light source section, in accordance with changes due to temperature in emission spectrums of the light emitting elements.

13. The device according to claim 10, wherein at least some of the light emitting elements have an emission spectrum corresponding to a red color component wavelength region, and when the original is a reversal film, the controller controls light emitting elements having an emission spectrum corresponding to a red color component wavelength region to shift in a direction towards shorter wavelengths, relative to when the original is a negative film.

14. The device according to claim 10, wherein, based on a type of the original, the controller determines desired overall spectral characteristics for light emitted from the light source section, and when the original is a specific type, the controller selectively illuminates light emitting elements corresponding to a specific color component wavelength region according to the desired spectral characteristics.

15. The device according to claim 9, wherein, when the original being read is a monochrome film, the controller either simultaneously illuminates each of light emitting elements of at least two different color component wavelength regions, or illuminates light emitting elements of only a specific single color component wavelength region.

16. The device according to claim 9, wherein the light source section is provided with a plurality of light source units each of which emits light having different spectral characteristics, and the controller illuminates different light source units in accordance with a type of the original being read.

17. The device according to claim 9, wherein light emitting elements are provided in the light source section corresponding to each color component wavelength region, and a light source unit is provided having light emitting elements corresponding to at least one color component wavelength region, with the light emitting elements in the light source unit each having a different emission spectrum.

18. The device according to claim 9, further comprising an image processor for performing image processing on image data obtained when the sensing apparatus outputs electrical signals from light received that has passed through or been reflected from an original under processing conditions that correspond to the controlling of the light source section by the controller.

19. The device according to claim 9, wherein the sensing apparatus
divides, into N color components, light which has been transmitted through or reflected by the original and has been incident on the sensing apparatus, and the sensing apparatus carries out sensing by using a charge-accumulating-type light sensor which accumulates charges corresponding to light amounts of respective color component lights, and the sensing apparatus has an accumulating time controller which controls the charge accumulating time at the charge-accumulating-type sensor in accordance with control of the light source section carried out by the controller.

20. A method for producing light for reading an original, wherein the light is either transmitted through an original to be read or reflected by the original, and thereafter, the light is separated into N color components, and electrical signals are produced, the method comprising the steps of:
forming a light source section from M light emitting elements each having a different emission spectrum, wherein $M>N$;
determining a type of the original, which will be read using emitted light from the light source section;
selecting desired overall spectral characteristics for light emitted from the light source section based on the type of the original; and
providing overall spectral characteristics for light emitted from the light source section by controlling at least one of whether each of the M light emitting elements is illuminated, emission intensity of each of the M light emitting elements, and emission time of each of the M light emitting elements, in accordance with the selected overall spectral characteristics.

21. The light source device according to claim 2, wherein the at least one of a type of spectral transmission density characteristics of the original and a type of spectral sensitivity characteristics of the recording material are calculated by the light source device.

22. The light source device according to claim 1, wherein the controller controls overall spectral characteristics of light emitted from the light source section by controlling emission intensity of each of the M light-emitting elements of the light source section.

23. The light source device according to claim 1, wherein the controller controls overall spectral characteristics of light emitted from the light source section by controlling emission time of each of the M light-emitting elements of the light source section.

* * * * *